Figure 1:
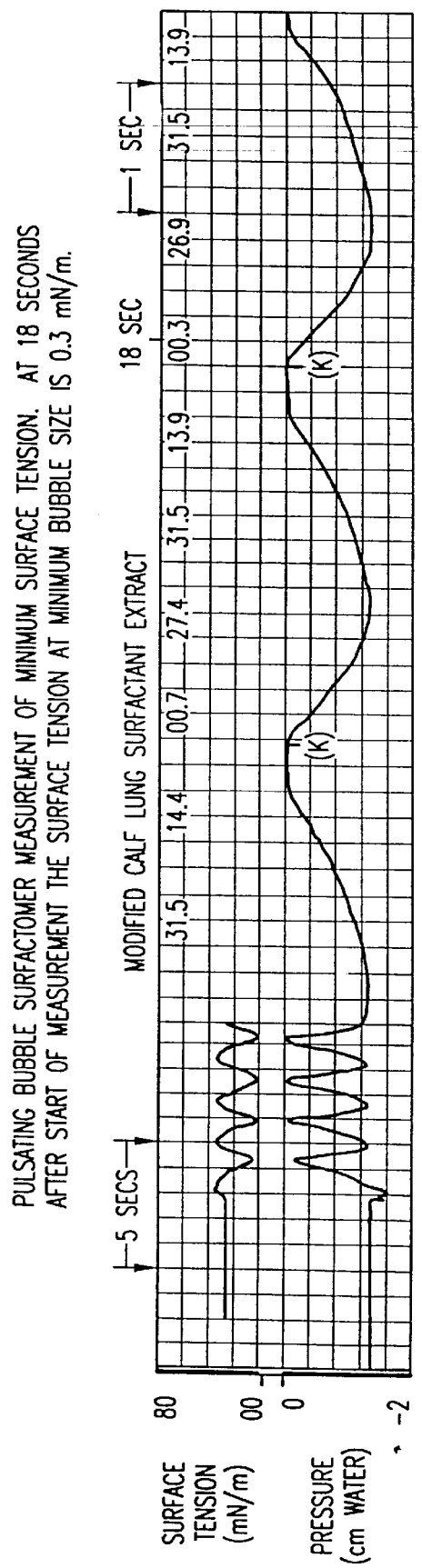

United States Patent [19]
Egan et al.

[11] Patent Number: 6,129,934
[45] Date of Patent: Oct. 10, 2000

[54] MODIFICATION OF ANIMAL LUNG SURFACTANT FOR TREATING RESPIRATORY DISEASE DUE TO LUNG SURFACTANT DEFICIENCY OR DYSFUNCTION

[75] Inventors: Edmund A. Egan, Amherst; Bruce A. Holm, Batavia; William H. Ferguson, Tonawanda, all of N.Y.

[73] Assignee: ONY, Inc., Amherst, N.Y.

[21] Appl. No.: 08/475,539

[22] Filed: Jun. 7, 1995

[51] Int. Cl.[7] .................................................. A61K 35/42
[52] U.S. Cl. .............................. 424/557; 514/21; 424/422
[58] Field of Search .................................... 424/422, 450, 424/434, 557; 514/21

[56] References Cited

U.S. PATENT DOCUMENTS

| | | | |
|---|---|---|---|
| 4,338,301 | 7/1982 | Tetsuro et al. | 424/95 |
| 4,397,839 | 8/1983 | Tanaka | 424/95 |
| 4,603,124 | 7/1986 | Takei et al. | 514/78 |
| 4,765,987 | 8/1988 | Bonte et al. | 424/450 |
| 5,013,720 | 5/1991 | Whitsett | 514/12 |
| 5,552,161 | 9/1996 | Disse et al. | 424/557 |

FOREIGN PATENT DOCUMENTS

| | | |
|---|---|---|
| 0 286 011 A2 | 10/1988 | European Pat. Off. . |
| 0 593 094 | 1/1989 | European Pat. Off. . |
| 2 050 832 | 6/1980 | United Kingdom . |
| WO 92/04907 | 4/1992 | WIPO . |

OTHER PUBLICATIONS

Egan et al., "Surfactant phospholipid, not protein, concentration is the limiting factor in lung surfactant biophysical activity", Am. Rev. Respir. Dis., 145:130A, 1992.

Wiswell et al., "Respiratory distress syndrome in the newborn: innovative therapies", American Family Physician, 47:407–414, 1993.

Adams, F., et al. "Effects of Tracheal Installation of Natural Surfactant in Premature Lambs" *Pediat. Res.* 12: 841–848 (1978).

Avery, Mary Ellen and Jere Mead. "Surface Properties in Relation to Atelectasis and Hyaline Membrane Disease" *AMA Journal of Diseases of Children* vol. 97: 517–523.

Bermel, M.S., McBride, J.T. and R.H. Notter. "Lavaged excised rat lungs as a model of surfactant deficiency" *Lung* 162: 99–113 (1984).

Bligh, E.G., and W.J. Driver. "A Rapid Method of Total Lipid Extraction and Purification" *Canadian Journal of Biochemistry and Physiology* vol. 37 No. 8: 911–917 (Aug. 1959).

Bloom, B., et al. "Human and Calf Lung Surfactant: A Comparison" *neonatal Intensive Care*: 31–35 (Mar./Apr. 1993).

Chen, P.S., Toribara, T.Y., and Huber Warner. "Microdetermination of Phosphorus" *Analytical Chemistry* 1756–1758.

Chu, J., et al. "Neonatal Pulmonary Ischemia Part I: Clinical and Physiological Studies" *Pediatrics* vol. 40, No. 4, Part II: 709–782 (Oct. 1967).

Collaborative European Multicenter Study Group. "Surfactant Replacement Therapy for Severe Neonatal Respiratory Distress Syndrome: An International Randomized Clinical Trial" *Pediatrics* vol. 82 No. 5: 683–691 (Nov. 1988).

Cummings, J., et al. "A Controlled Clinical Comparison of Four Different Surfactant Preparations in Surfactant–deficient Preterm Lambs" *Am Rev Respir Dis:* 999–1004 (1992).

Enhorning, G. and Bengt Robertson. "Lung Expansion in the Premature Rabbit Fetus After Tracheal Deposition of Surfactant" *Pediatrics* vol. 50, No. 1: 58–66 (Jul. 1972).

Enhorning, G. "Pulsating bubble technique for evaluating pulmonary surfactant" *J. Appl. Physiol.: Respirat.Environ. Exercise Physiol.* 43(2): 198–203 (1977).

Ferro, P. and Anna Bell Ham. "Rapid Determination of Total and Free Cholesterol in Serum" *American Journal of Clinical Pathology* vol. 33, No. 6: 545–549 (Jun. 1960).

Fujiwara, T., et al. "Artificial Surfactant Therapy in Hyaline–Membrane Disease" *The Lancet Ltd.:* 55–59 (Jan. 12, 1980).

Hall, S., et al. "Importance of Hydrophobic Apoproteins as Constituents of Clinical Exogenous Surfactants" *Am Rev Respir Dis* 145: 24–30 (1992).

Holm, B., Enhorning, G. and R.H. Notter. "A biophysical mechanism by which plasma proteins inhibit lung surfactant activity" *Chemistry and Physics of Lipids* 49: 49–55 (1988).

Hudak, M., et al. "Infasurf V. Exosurf for the Prophylaxis of RDS: A Ten Center Randomized Double–Masked Comparison Trial" *Pediatric Research* 1369 (1994).

Hudak, M., et al. "Infasurf V. Exosurf for the Treatment of RDS: A 21 Center Randomized Double–Masked Comparison Trial" *Pediatric Research* 1370 (1994).

Kattwinkel, J., et al. "Prophylactic Administration of Calf Lung Surfactant Extract is More Effective Than Early Treatment of Respiratory Distress Syndrome in Neonates of 29 Through 32 Weeks' Gestation" *Pediatrics* vol. 92, No. 1: 90–98 (Jul. 1993).

(List continued on next page.)

*Primary Examiner*—Marian C. Knode
*Assistant Examiner*—Brenda G. Brumback
*Attorney, Agent, or Firm*—Dorsey & Whitney LLP

[57] ABSTRACT

The present invention relates to the method of using a composition of matter that maintains the biophysical and physiological characteristics of natural surfactant, including the rapid and spontaneous adsorption of dilute suspensions to an air-liquid interface; the generation of low surface tension (<2.1 mN/m) at a surface area compression of 50% by the pulsating bubble method of Enhorning; and the restoration of greater than 75% of the lost volume of a surfactant deficient lung as determined by the method of Bermel. The material is produced by adding disaturated phospholipid to the extract of surface active material obtained by lavage of the air space of the lungs of animals. The material contains 90–96% phospholipid, 0–6% cholesterol, and 1–3% protein. Greater than 99% of the protein is lung surfactant apoproteins B & C. A sterile pharmaceutical preparation of the surface active material can be used for treating diseases caused by deficiency or dysfunction or natural lung surfactant.

83 Claims, 2 Drawing Sheets

OTHER PUBLICATIONS

Kendig, J., et al. "Surfactant Replacement Therapy at Birth: Final Analysis of a Clinical Trial and Comparisons With Similar Trials" *Pediatrics* vol. 82, No. 5: 756–762 (Nov. 1988).

Kendig, J., et al. "A Comparison of Surfactant as Immediate Prophylaxis and as Rescue Therapy in Newborns of Less than 30 Weeks' Gestation" *The New England Journal of Medicine* vol. 324, No. 13: 865–871 (Mar. 28, 1991).

Kwong, M., et al. "Double–Blind Clinical Trial of Calf Lung Surfactant Extract for the Prevention of Hyaline Membrane Disease in Extremely Premature Infants" *Pediatrics* vol 76, No. 4: 585–592 (Oct. 1985).

Lewis, J. and Alan Jobe. "Surfactant and the Adult Respiratory Distress Syndrome" *Am Rev Respir Dis* vol. 147: 218–233 (1993).

Lowry, O., et al. "Protein Measurement With the Folin Phenol Reagent" pp. 265–275.

Mason, R., Nellenbogen, J. and John A. Clements. "Isolation of disaturated phosphatidylcholine with osmium tetroxide" *Journal of Lipid Research* vol. 17, *Notes on Methodology:* 281–284 (1976).

McLean, L., et al. "An Amphipathic α–Helical Decapeptide in Phosphatidylcholine Is an Effective Synthetic Lung Surfactant" *Am Rev Respsir Dis* vol. 147: 462–465 (1993).

Metcalfe, L., Enhorning, G. and Fred Possmayer. "Pulmonary surfactant–associated proteins: their role in the expression of surface activity" *the American Physiological Society:* 34–41.

Morley, C.J., et al. "Dry Artificial Lung Surfactant and its Effect on Very Premature Babies" *The Lancet:* 64–68 (Jan. 10, 1981).

Notter, R. and Donald L. Shapiro. "Lung Surfactants for Replacement Therapy: Biochemical, Biophysical, and Clinical Aspects" *Clinics in Perinatology* vol. 14, No. 3: 433–479 (Sep. 1987).

Peterson, Gary L., "A Simplification of the Protein Assay Method of Lowry et al. Which is More Generally Applicable" *Analytical Biochemistry* 83: 346–356 (1977).

Robillard, E., et al. "Microaerosol Administration of Synthetic β–γ–Dipalmitoyl–L–α–Lecithin in the Respiratory Distress Syndrome: A Preliminary Report" *Canad. Med. Ass.J.* vol. 90: 55–57 (Jan. 11, 1964).

Smyth, J.A., et al. "Hyaline Membrane Disease Treated with Bovine Surfactant" *Pediatrics* vol. 71 No. 6: 913–917 (Jun. 1983).

Yu, S., et al. "Bovine Pulmonary Surfactant: Chemical Composition and Physical Properties" *Lipids* vol. 18, No. 8: 522–529 (1983).

Tabak, S.A. and R.H. Notter "Modified technique for dynamic surface pressure and relaxation measurements at the air–water interface" *Rev. Sci. Instrum.* vol. 48, No. 9: 1196–1201 (Sep. 1977).

Schurch, S., et al. "A captive bubble method reproduces the in situ behavior of lung surfactant monolayers" *the American Physiological Society:* 2389–2396.

Holm, B., et al. "Biophysical inhibition of synthetic lung surfactants" *Chemistry and Physics of Lipids* 52: 243–250 (1990).

Egan, E. and B.A. Holm. "Surfactant Phospholipid, Not Protein, Concentration is the Limiting Factor in Lung Surfactant Biophysical Activity" *American Review of Respiratory Disease* 145:A130 (1992).

Berggren, P. et al. "Physiological Activity of Pulmonary Surfactant with Low Protein Content: Effect of Enrichment with Synthetic Phospholipids" *Experimental Lung Research,* vol. 8, No. 1, pp. 29–51, 1985.

Holm, B. et al. "Content of Dipalmitoyl Phosphatidylcholine in Lung Surfactant: Ramifications for Surface Activity" *Pediatric Research,* vol. 39, No. 5, pp. 805–811, 1996.

Tokyo Tanabe Research Laboratory, et al., "Preparation of Lung Surfactant and its Chemical Composition and Surface Activities", *J. Jap. Med. Soc. Biol. Interface 13* (2), 27–34 (1982), 27 pages.

Tokyo Tanabe Research Laboratory, et al., "Relation between the Constituting Components and Surface Activity of Lung Surfactant", *J. Jap. Med. Soc. Biol. Interface 13* (2), 35–42 (1982), 22 pages.

Tokyo Tanabe Research Laboratory, et al., "Reconstitution of Lung Surfactant by Adjusting the Chemical Composition", *J.Jap. Med. Soc. Biol. Interface 13* (2), 43–50 (1982), 29 pages.

MODIFICATION OF ANIMAL LUNG SURFACTANT FOR TREATING RESPIRATORY DISEASE DUE TO LUNG SURFACTANT DEFICIENCY OR DYSFUNCTION

TABLE OF CONTENTS

1. INTRODUCTION
2. BACKGROUND OF THE INVENTION
   2.1. The Role of Surfactant in Pulmonary Physiology
   2.2. Surfactant Deficiency or Dysfunction
   2.3. Developments in Surfactant Replacement Therapy
   2.4. Sources of Surfactant
   2.5. Methods of Preparation
   2.6. Treatment with CLSE
   2.7. Recent Developments in Surfactant Replacement Products
3. SUMMARY OF THE INVENTION
   3.1. Definitions of Abbreviations
   3.2. New Composition of Matter and Methods for Producing the Same
4. BRIEF DESCRIPTION OF THE DRAWINGS
   4.1. Surface Tension
   4.2. Pressure-Volume Mechanics
5. DETAILED DESCRIPTION OF THE PREFERRED EMBODIMENTS OF THE INVENTION
   5.1. Chemical Composition
      5.1.1. Phospholipid Content
      5.1.2. Protein Content
      5.1.3. Cholesterol Content
   5.2. Biophysical Properties
      5.2.1. Adsorption Properties at a Gas-Liquid Interface
      5.2.2. Surface Tension Reducing Capacity
      5.2.3. Restoration of Lung Pressure-Volume Mechanics
   5.3. Preparation of The Extracted Surface Active Material
      5.3.1. Collection of Surface Active Material
         5.3.1.1. Concentration of Isolated Surface Active Material
      5.3.2. Extraction and Isolation of Surface Active Material
   5.4. Augmentation of Extracted Surface Active Material
   5.5. Removal of Organic Solvent From Augmented Surface Active Material
   5.6. Resuspension of Augmented Surface Active Material in Aqueous Solution
      5.6.1. Sterilization of the Resuspension of Augmented Surface Active Material
   5.7. Pharmaceutical Product
   5.8. Administration of Augmented Surface Active Material
   5.9. Therapeutic Uses
      5.9.1. Prophylaxis for Premature Infants at Birth
      5.9.2. Treatment of Patients with Respiratory Distress Syndromes
      5.9.3. Treatment of Patients with Acute Respiratory Failure
      5.9.4. Treatment of Patients with Lung Inhalation Injuries
      5.9.5. Prophylaxis of Patients at Risk of Acute Lung Disease
      5.9.6. Therapy for Obstructive Syndrome of Small Airways
6. EXAMPLES
   6.1. Recovery of Surface Active Material from Bovine Lungs by Lavage
   6.2. Extraction of Surface Active Material
   6.3. Addition of Exogenous Phospholipid to the Extracted Surface Active Material in Organic Solvent
   6.4. Resuspension of Extracted Surface Active Material With or Without Exogenous Phospholipids
   6.5. Addition of Exogenous Phospholipid to the Extracted Surface Active Material in Aqueous Medium
   6.6. Biophysical Assays
   6.7. Physiological Assays
      6.7.1. Physiological Assays in Excised Lungs
      6.7.2. Physiological Assays in Premature Mammals
   6.8. Administration of Augmented Surface Active Material
      6.8.1. General
      6.8.2. Preparing a Dose of the Augmented Surface Active Material
      6.8.3. Preparing a Recipient for a Dose of the Augmented Surface Active Material
      6.8.4. Administration of the Augmented Surface Active Material By Instillation
      6.8.5. Administration of the Augmented Surface Active Material By Aerosol
   6.9. Use as a Pharmaceutical Agent
      6.9.1. Prophylaxis Treatment at Birth For Infants at High Risk for Respiratory Distress Syndrome (RDS)
      6.9.2. Treatment of Patients With Respiratory Failure From Respiratory Distress Syndromes (RDS)
      6.9.3. Treatment of Patients With Respiratory Failure from Other Lung Diseases
      6.9.4. Treatment of Patients With Inhalation Injury to the Lung
      6.9.5. Prophylaxis by Instillation of Lung Surfactant Into Patients at High Risk For Respiratory Disease Due to Lung Surfactant Inactivation or Injury to Type II Alveolar Cell Activity
      6.9.6. Treatment of Obstructive Syndromes of Small Airways
7. CLAIMS

1. INTRODUCTION

This invention relates to (1) a composition of matter having the biophysical and physiological activities of natural lung surfactant, (2) a pharmaceutical product useful for treating respiratory disease due to lung surfactant deficiency or dysfunction, and (3) the methods for producing the composition of matter and the pharmaceutical product.

2. BACKGROUND OF THE INVENTION

2.1. The Role of Surfactant in Pulmonary Physiology.

Inhaled air containing oxygen travels through the trachea, the bronchi, and the bronchioles to the hundreds of millions of terminal alveoli. The terminal alveoli are the air spaces in the lungs where oxygen is taken up by the blood in exchange for carbon dioxide.

At the interface between the gas in the terminal alveoli and the liquid of the lung tissue, (i) oxygen diffuses into the blood from the alveoli and (ii) carbon dioxide diffuses from the blood to the alveolar air before being exhaled. To diffuse from the alveolar gas to the blood, an oxygen molecule must traverse the liquid lining the alveoli, at least one epithelial cell, the basement membrane, and at least one endothelial cell.

In order to attain sufficient uptake of oxygen by the blood and excretion of carbon dioxide from the blood, an animal's lungs must ventilate the terminal alveoli simultaneously and evenly. Either unsynchronized or uneven ventilation will prevent sufficient oxygen uptake into the circulating blood and result in the retention of carbon dioxide in the body.

Pulmonary surfactant acts at the interface between alveolar gas and the liquid film lining the luminal surface of the cells of the terminal alveoli. The normal pulmonary surfactant lining is extremely thin, usually no more than 50 nm thick. Thus, the total fluid layer covering the 70 square meters of alveolar surface in an adult human is only 35 ml.

For materials to be effective lung surfactants, surfactant molecules must move rapidly to the surface of the liquid. Pulmonary surfactant functions by adsorbing to the surface of the liquid covering these lining cells and changing surface tension of the alveolar fluid during the respiratory cycle.

Surface tension is a characteristic of most liquid solutions. At the interface between liquid and a gas phase, the movement of molecules at the surface of the liquid is restricted by intermolecular forces acting on those molecules. The intermolecular forces have a net direction that tends to decrease the area of the surface. The net force at the surface is referred to as surface tension. Surface tension varies with molarity, temperature and multiple solutes. Surface tension has units of force per unit length (dynes/cm or mN/m). The vector of the surface tension force is perpendicular to the plane of the interface.

The lungs of vertebrates contain surfactant, a complex mixture of lipids and protein which causes surface tensions to rise during surface expansion (inflation) and decrease during surface compression (deflation). During lung deflation, surfactant decreases surface tension to near $\leq 1$ mN/m, so that there are no surface forces that would otherwise promote alveolar collapse. Aerated alveoli that have not collapsed during expiration permit continuous $O_2$ and $CO_2$ transport between blood and alveolar gas and require much less force to inflate during the subsequent inspiration. During inflation, lung surfactant increases surface tension as the alveolar surface area increases. A rising surface tension in expanding alveoli opposes over-inflation in those airspaces and tends to divert inspired air to less well-aerated alveoli, thereby facilitating even lung aeration.

2.2. Surfactant Deficiency or Dysfunction.

Although the exact composition and physical characteristics of natural lung surfactant have not been determined, material isolated from the lumen of lungs, termed natural surfactant, contains a mixture of phospholipids, neutral lipids, and proteins. (Jobe A, Ikegami M, Surfactant for the treatment of respiratory distress syndrome. Am Rev Respir Dis, 1987; 136:1256–75). The phospholipids are not specific to surfactant, but are also present in other biologic materials, particularly membranes. The predominant phospholipids in surfactant, however, are disaturated phosphatidylcholines which are present in low concentrations in most membranes. Among the proteins found in the lung lumen are mucoproteins, plasma proteins, and lung specific apo-proteins.

The alveoli are lined with epithelial cells that have a role in producing surfactant, maintaining the activity of surfactant, and preventing the inactivation of surfactant. The epithelial cells form a continuous, tight barrier that normally prevents entry into the alveoli of molecules from the circulation that can inhibit surfactant.

The alveolar epithelium consists of a least two types of alveolar cells, referred to as type I and type II alveolar cells. The type II alveolar cells normally synthesize both the phospholipids and apo-proteins that are in lung surfactant, store newly synthesized material in the intracellular inclusion bodies, secrete the surfactant into the alveolar space, absorb surfactant from the alveolar space, and metabolize material reincorporated into the type II cell. The role of type I cells in surfactant function has not yet been identified.

Lung surfactant is normally synthesized at a very low rate until the last six weeks of fetal life. Human infants born more than six weeks before the normal term of a pregnancy have a high risk of being born with inadequate amounts of lung surfactant and inadequate rates of surfactant synthesis. The more prematurely an infant is born, the more severe the surfactant deficiency is likely to be. Severe surfactant deficiency can lead to respiratory failure within a few minutes or hours of birth. The surfactant deficiency produces progressive collapse of alveoli (atelectasis) because of the decreasing ability of the lung to expand despite maximum inspiratory effort. As a result, inadequate amounts of oxygen reach the infant's blood.

Endogenous surfactant production typically accelerates after birth, even in quite premature infants. If the infant survives the first few days, lung surfactant status generally becomes adequate.

Additional causes of respiratory failure from surfactant dysfunction have been reported due to defects in surfactant synthesis (congenital apo-protein B deficiency), or in secretion or metabolism of surfactant (alveolar proteinosis). In addition, lung surfactant can be inhibited and inactivated in vitro by a variety of proteins, cell wall phospholipids, enzymes, and other products of inflammatory responses.

Injury to juvenile and adult animals can also inactivate surfactant and produce a respiratory failure with a similar pathophysiology to the surfactant deficiency in premature infants. This respiratory failure is often referred to as the Adult (or Acute) Respiratory Distress Syndrome, ARDS. This syndrome results from several simultaneous pathologic processes, one of which is a generalized inhibition of the extracellular surfactant in the alveolar space plus dysfunction of the type II alveolar cells which adversely affect the synthesis, secretion, or metabolism of surfactant.

Current treatment of respiratory failure includes supplementation of oxygen, mechanical ventilation, and instillation or aerosolization of materials with lung surfactant activity. Some patients die from respiratory failure despite current treatments, some survive with permanently damaged lungs, and other patients recover after prolonged therapy.

2.3. Developments in Surfactant Replacement Therapy.

Deficiency of lung surfactants results from either (1) premature birth before the fetus has produced adequate lung surfactant or (2) the metabolic alteration of the lung's type II cells by lung disease, thereby preventing the secretion of an effective lung surfactant. Further, extracellular alveolar surfactant can be inhibited when it interacts with inflammatory cells, proteins, enzymes, cytokines and other substances which accumulate in lung alveoli in lung disease and by injury. Altered surfactant metabolism may also decrease the amount or activity of extracellular alveolar surfactant.

In 1959, Mary Ellen Avery and Jere Mead reported the results of a study of premature infants with clinical symptoms of progressive atelectasis and the pathologic diagnosis of hyaline membrane disease at autopsy. Avery and Mead demonstrated that the Respiratory Distress Syndrome ("RDS") identified in these premature infants was caused by a deficiency in lung surfactant. (Avery ME, Mead J: Surface properties in relation to atelectasis of hyaline membrane disease. Am J Dis Child 1959; 97:517–23.)

The discovery that RDS was a deficiency disease provoked two clinical trials of replacement therapy using aerosol administration of dipalmitoylphosphatidylcholine, DPPC, into the incubators of premature infants with RDS. DPPC was thought by the trial investigators to be the principal active component of natural surfactant. Neither study produced positive clinical results. (Robillard E, Alarie Y, Dagenais-Perusse P, et al.: Microaerosol administration of synthetic dipalmitoyl lecithin in the respiratory distress syndrome: a preliminary report. Can Med Assoc J, 1964; 90:55–57; Chu J, Clements JA, Cotton EK, et. al.: Neonatal pulmonary ischemia: clinical and physiological studies. Pediatrics 1967; 40:709–82.) The conclusion of these studies was that RDS was not treatable by surfactant replacement therapy.

In the 1970's, Enhorning and Robertson in Sweden and Adams and colleagues in the United States demonstrated conclusively that lung surfactant lavaged from lungs of adult animals could induce improved ventilation and gas exchange when instilled into the lungs of premature, surfactant-deficient animals. (Enhorning G, Robertson B: Lung expansion in the premature rabbit fetus after tracheal deposition of surfactant. Pediatrics 1972: 50:58–66; Adams FH, Towers B, Osher AB et. al.: Effects of tracheal instillation of natural surfactant in premature lambs. I. Clinical and autopsy findings. Pediatric Research 1978; 12:841–48.)

In 1980, Fujiwara and colleagues in Japan and Morely and colleagues in Britain reported that clinical improvement followed instillation of surfactant preparations into the lungs of premature infants. (Fujiwara T, Maeta H, Chida S, et. al.: Artificial surfactant therapy in hyaline membrane disease. Lancet 1980; 1:55–9; Morley CJ, Bangham AD, Miller N, et. al.: Dry artificial lung surfactant and its effect on very premature babies. Lancet 1981; 1:64–8.) Fujiwara and his colleagues used an extract of lung mince, and Morley and his colleagues used a powder of phospholipids alone. Both groups, however, delivered their replacement material into the lungs directly and did not use the aerosol methodology of the 1960's.

In 1980, Metcalfe, Possmayer, and Enhorning reported that an organic extract of lung surfactant recovered from lavage of bovine lungs had biophysical properties equal to natural lung surfactant. (Metcalfe IL, Enhorning GE, Possmayer F. Pulmonary surfactant associated proteins: their role in the expression of surface activity. J Appl Physiol 1980; 49:34–41.) The organic extract used in these studies contained the hydrophobic, proteolipid surfactant apoproteins SP-B and SP-C and the phospholipids of natural surfactant but did not contain the apo-protein SP-A. Unlike natural surfactant, the organic extract did not lose physiological activity when heated to temperatures greater than 100° C.

These studies generated new interest in treating premature, surfactant-deficient animals with exogenous lung surfactant. The characteristics of the extract used in these studies was extensively investigated in Wilhelmy balances, pulsating bubble surfactometers, excised surfactant deficient rat lungs, premature rabbits, and premature lambs. These investigations revealed that the biophysical properties and biologic activities extract equaled or exceeded the biophysical properties and biologic activity of natural surfactant. This information was summarized in a 1987 review by Notter and Shapiro. (Notter RH and Shapiro DL. Lung surfactant for replacement therapy: biochemical biophysical and clinical aspects. Clinics Perinatology 1987; 14:433–79.)

2.4. Sources of Surfactant.

Since the 1950's, lung surfactant has been obtained from all vertebrates that breathe air: for example, lung fish, amphibians, reptiles, and every order of mammals, including humans. Surface active material may be recovered from the air spaces of the lungs of animals by lavage or by mincing whole lung tissue. Organic soluble material recovered from the lavage includes lipids and two apoproteins, SP-B and SP-C, proteins and water. Water soluble materials recovered from the lavage contain apo-protein A, mucoproteins, serum proteins and carbohydrates. Raw material obtained from lungs and so recovered, whether by lavage of the air space or by mincing whole lung tissue, is an unpurified, complex material which contains substances in addition to lung surfactant. Surface active material obtained by mincing whole lung tissue contains more non-surfactant substances than surface active material obtained by lavage of the air space.

Biologic materials that contain tissue elements, including neurons, may contain high concentrations of transmissible spongiform encephalopathy agents referred to as prions. Since a lung lavage does not contain measurable tissue, it is unlikely that unprocessed lung surfactant derived from a lavage of an infected animal could pass prions to recipient animals or humans. Moreover, the processing of the lavage pellet using a neutral 2:1 chloroform methanol extraction has the effect of decreasing the amount of any prions by a factor of by 99.9999%. (Safar J, Ceroni M, Piccardo P, et al. Subcellular distribution and physio-chemical properties of scrapie-associated precursor protein and relationship with scrapie agent. Neurology 1990; 40:503–8; ONY, Inc. (study on file).) This is a large additional margin of safety for a potential adverse effect of lung surfactant extract administration.

The part of the unpurified surfactant material recovered by lavage of the airspace that is soluble in organic solvents can be isolated by extraction. This material, when resuspended in physiological saline will improve the lung compliance, arterial oxygenation, and survival of premature, surfactant-deficient lambs as described by Cummings and colleagues. (Cummings JJ, Holm BA, Hudak ML, Hudak BB, Ferguson WH, Egan EA: Controlled clinical comparison of four different surfactant preparations in surfactant-deficient preterm lambs. Am Rev Respir Dis 1991; 145:999–1004.)

2.5. Methods of Preparation.

Previous surfactant products have been prepared in the following manner:

(1) Artificial Surfactants: Preparations containing only chemically defined components: phospholipid, alcohol, emulsifiers, fatty acids, triglycerides, or detergent. (Tooley WH, Clements JA, Muramatsu K, et al. Lung function in prematurely delivered rabbits treated with a synthetic surfactant. Am Rev Respir Dis, 1987; 136:651–6; Norley CJ, Bangham AD, Miller N, et al.: Dry artificial lung surfactant and its effect on very premature babies. Lancet 1981; 1:64–8.)

(2) Natural Surfactant: Surface active material obtained from the lavage of airspaces or amniotic fluid. (King RJ and Clements JA.

Surface active materials from dog lung. I. Methods of isolation.

II. Composition and physiological correlations. III. Thermal analysis. Am J Physiol 1972; 223:707–33; Enhorning G, Robertson B: Lung expansion in the premature rabbit fetus after tracheal deposition of surfactant, Pediatrics 1972: 50:58–66; Jobe A, Ikegami M, Glatz T et al. Duration of treatment of premature lambs with natural surfactant. J Clin Invest 1981; 67:370–5;

Hallman M, Merritt TA, Schneider H, et al. Isolation of human surfactant from amniotic fluid and a pilot study of its efficacy in respiratory distress syndrome. Pediatrics, 1983; 71:473–82.)

(3) Lung Tissue Surfactants: Surface active material obtained from preparations of whole lung tissue. (King RJ and Clements JA. Surface active materials from dog lung. I. Methods of isolation. II. Composition and physiological correlations. III. Thermal analysis. Am J Physiol 1972; 223:707–33.)

(4) Lung Tissue Surfactant Extracts: organic extracts of lung tissue resuspended in aqueous medium with or without additives. (King RJ and Clements JA. Surface active materials from dog lung. I.

Methods of isolation. II. Composition and physiological correlations. III. Thermal analysis. Am J Physiol 1972; 223:707–33; Fujiwara T, Maeta H, Chida S, et al.: Artificial surfactant therapy in hyaline membrane disease. Lancet 1980; 1:55–9.)

(5) Recombinant Surfactants: artificial surface active material having a peptide component of synthetic origins. (Cochrane CG, Revak SD,. Pulmonary surfactant protein B (SP-B): Structure function relationships. Science 1991; 254:566–8.)

(6) Natural Surfactant Extracts: Organic extracts of natural surface active material resuspended in an aqueous medium containing no tissue or additives. (Metcalfe IL, Enhorning GE, Possmayer F. Pulmonary surfactant associated proteins: their role in the expression of surface activity. J Appl Physiol 1980; 49:34–41; Egan EA, Notter RH, Kwong MS, Shapiro DL: Natural and artificial lung surfactant replacement therapy in premature lambs. J. Appl. Physiology, 1983; 55:875–83; Smythe JA, Metcalfe IL, Diffty P, et al.: Hyaline membrane disease treated with bovine surfactant. Pediatrics 1983; 71:913–7.)

2.6. Treatment with CLSE.

In 1982, six infants with RDS were treated at Hospital for Sick Children in Toronto with a single dose of organic extract surfactant (now called bovine Lung Extract Surfactant (bLES), produced at the University of Western Ontario in London, Ontario. The respiratory status of five of the six infants improved. (Smyth JA, Metcalfe IL, Duffty P et. al.: Hyaline membrane disease treated with bovine surfactant. Pediatrics 1983; 71:913–7.)

In the 1980's, three initial randomized, double masked, placebo controlled clinical trials were initiated using bovine lavage lung surfactant extracts as a single prophylaxis dose of 100 mg/kg administered at birth to premature infants $\leq 29$ weeks gestation. Two trials, one in Buffalo and one in Rochester, used Calf Lung Surfactant Extract (CLSE), produced at the University of Rochester. (Kwong MS, Egan EA, Notter RH et. al.: Double blind clinical trial of calf lung surfactant extract for the prevention of hyaline membrane disease in extremely premature infants. Pediatrics 1985; 76:585–92; Kendig JW, Notter RH, Cox C, et. al.: Surfactant replacement therapy at birth: final analysis of a clinical trial and comparisons with similar trials. Pediatrics 1988; 82:756–82.) The third trial in Toronto used bLES. (Enhorning G, Sheenan A, Possmayer F, et. al.: Prevention of neonatal respiratory distress syndrome of tracheal instillation of surfactant: a randomized clinical trial. Pediatrics 1985; 76:145–53.)

All three trials had positive results. The incidence and severity of RDS were lower in the CLSE/bLES treated groups than in the control groups. Clinical studies with bLES have continued in Canada, and clinical studies with CLSE have continued in the United States. Clinical studies with bovine extract surfactants have continued to enlarge the knowledge of the optimal methods for administering surfactant replacement.

Prospective, controlled scientific clinical trials have demonstrated that viable premature infants born 8–17 weeks before the normal end of gestation will have a lower incidence of respiratory failure and a lower death rate from respiratory failure when treated with surfactant than infants not treated at birth, even if the infants not treated at birth are treated after respiratory disease is evident.

Treatment at birth with CLSE provides more effective and longer sustained physiological activity in surfactant deficient premature animals than species-specific natural surfactant or lung surfactant products approved for human use by the United States Food & Drug Administration. (Hudak ML, Matleson EJ, Baus JA et al. Infasurf v. Exosurf for Prophylaxis of RDS: A Five Center Randomized Double-Masked Comparison Trial. Ped Res 35:231A, 1994; Hudak ML, Matleson EJ, Baus JA et al. Infasurf v. Exosurf for Treatment of RDS: A 21 Center Randomized Double-Masked Comparison Trial, Ped Res: 35:231A, 1994; Bloom BT, Delmore P Katlwinkel Jet. Al: Raldomized Double Blind Multicenter Trial of Survanta and Infasurf. Ped Res: 35:326A, 1994; Cummings JJ, Holm BA, Hudak ML, Hudak BB, Ferguson WH & Egan EA: Controlled clinical comparison of four different surfactant preparations in surfactant-deficient preterm lambs. Am Rev Respir Dis, 1991; 145:999–1004.) This superior activity and longer sustained effect is consistent with the superior biophysical properties of CLSE compared to other pharmacologic surfactant preparations.

In addition, the superior activity of CLSE compared to natural surfactant can be attributed to the absence of surfactant apoprotein A from CLSE. Surfactant apoprotein A is present in natural surfactant preparations and has been shown to accelerate the re-uptake of surfactant into the Type II alveolar cells. The re-uptake of surfactant shortens the surface active effect.

2.7. Recent Developments in Surfactant Replacement Products.

Based on the success of treatment with CLSE, it became desirable to modify the CLSE to obtain similar biophysical and biologic properties while increasing the amount of drug product that can be prepared from a specific amount of material extracted from a calf lung.

Investigations into critical elements of lung surfactant integrity by Egan and colleagues had shown that the concentration of apoproteins was critical for spontaneous adsorption activity and that concentration of phospholipid was critical for minimum surface tension lowering activity. (Egan EA, Holm BA: Surfactant phospholipid, not protein, concentration is the limiting factor in lung surfactant biophysics. Am Rev Respir Dis 1992; 145:130A.) Hall and colleagues showed that organic extract material itself was superior in biophysical properties and in restoring mechanical properties of surfactant deficient excised lungs to both purely synthetic surfactant and natural organic extract surfactant with added phospholipids. (Hall SB, Venkitaraman AR, Whitsett JA, et al.: Importance of hydrophobic apoproteins as constituents of clinical exogenous surfactants. Am Rev Respir Dis, 1992; 145:24–30.)

Hall and colleagues also concluded that adding lung surfactant apoproteins to phospholipids appeared to be the preferred method of improving activity in contrast to adding additional phospholipid to surface active extracts. For example, studies demonstrated no improvement in biophysical or physiologic activity after further addition of phospholipid to organic extracts of lung tissue which had already been supplemented with phospholipid. Evaluation of future directions for surfactant replacement products by Lewis and Jobe concluded that the focus should be to develop preparations with high protein contents and containing more of the apoproteins. (Lewis JF, Jobe AH: Surfactant and the adult respiratory distress syndrome. Am Rev Respir Dis 1993; 147:218–33.) Moreover, since proteins are viewed as the activity limiting component of surface active products, the activity of surface active products would be limited by low protein concentrations. (Mizuno K, Ikegami M, Chen CM, et al. Surfactant protein-B supplementation improves in vivo function of a modified natural surfactant. Pediatric Res 1995; 37:271–6.)

Contrary to the conclusions reached from data in previous studies, the composition of this invention (a) increases the amount of drug product that can be prepared from a specific amount of material extracted from calf lung and (b) obtains biophysical and biological properties similar to CLSE by increasing the concentration of disaturated phospholipids.

3. SUMMARY OF THE INVENTION

3.1. Definitions of Abbreviations.

As used in this description, the following abbreviations have the following meanings:
S ARDS—Adult (or Acute) Respiratory Distress Syndrome
°C.—degrees celsius
cm—centimeter
DPPC—dipalmatoylphosphatidylcholine
g—gravity
>—greater than
$H_2O$—molecular abbreviation for water
kg—kilogram
<—less than
l—liter
LPC—lysophosphatidylcholine
m—meter
µl—microliter
µm—micrometer (micron)
mg—milligram
min—minute
ml—milliliter
mm—millimeter
mM—milliMolar
mN—milliNewton
N—Newton
PBS—pulsating bubble
PC—phosphatydilcholine
PC/DS—phosphatidylcholine—disaturated
PE—phosphatydilethanolamine
PG—phosophatidylglycerol
pH—negative logarithm of hydrogen ion concentration
PI—phosphatidylinositol
PL—phospholipid
RDS—Respiratory Distress Syndrome
rpm—revolutions per minute
SPH—sphingomyelin
SN-1—position 1 of glycerol molecule
SN-2—position 2 of glycerol molecule
vol—volume

3.2. New Composition of Matter and Methods for Producing the Same.

The invention is a new composition of matter, which reduces minimum surface tension to <2.1 mN/m and restores pressure-volume relationships in surfactant deficient excised lungs, that was developed by combining the organic-soluble extract of mammalian lung lavage material with additional disaturated phospholipids. The new composition has the biophysical properties and physiological activity of natural lung surfactant (and its organic extracts) at lower total protein concentrations than can be achieved with unmodified material. The new material can be used in the treatment of diseases caused by lung surfactant deficiency or lung surfactant dysfunction. The invention also includes the method of making the new material, including the sterilization of the new material to facilitate its use as a pharmaceutical product.

According to one object of the present invention the relative composition of the hydrophobic extract of lung lavage is changed by increasing the concentration of disaturated phospholipids from 45–60% to 55–80% of the total amount of phospholipids.

According to another object of the present invention, the minimum surface tension of the material is less than 2.1 mN/m at a surface area compression of 50% by the pulsating bubble method of Enhoming at total lipid concentrations of less than 10 mg/ml.

According to another object of the present invention there is provided a method for maintaining the biophysical and physiologic properties of the CLSE at higher dilutions (lower concentrations) of total surfactant apoprotein B and apoprotein C than are possible with other surfactant preparations.

According to another object of the present invention there is provided a method for suspending the new material in an aqueous solution by using a combination of mechanical and thermal energy.

According to another object of the present invention there is provided a method for sterilizing the new material by using heat.

According to another object of the present invention, the composition of matter can be used to treat respiratory disease in animals.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the attributes particularly pointed out in the appended claims.

4. BRIEF DESCRIPTION OF THE DRAWINGS

4.1. Surface Tension.

[FIG. 1]

FIG. 1 shows a bubble surfactometer tracing of the composition of the invention at a concentration of 3 mg/ml two minutes after a bubble had been created and was oscillating at 20 cycles/min between radii of 0.40 and 0.55 mm. The notch (K) indicates minimum bubble radius. The ordinate on the figure is pressure in cm $H_2O$ and the abscissa is time in seconds. The alpha numeric on the top is calculated surface tension using the LaPlace equation at the time of the alpha numeric.

$$\Delta P = \frac{2\gamma}{R}$$

Where $\gamma$ is surface tension, $\Delta P$ is the change in pressure across the interface, and R is the radius of the bubble.

At the notch, corresponding to minimum surface area, surface tension is 0.7 and 0.3 mN/m in the two pulsations in this trace.

4.2. Pressure-Volume Mechanics.

Figure 2:
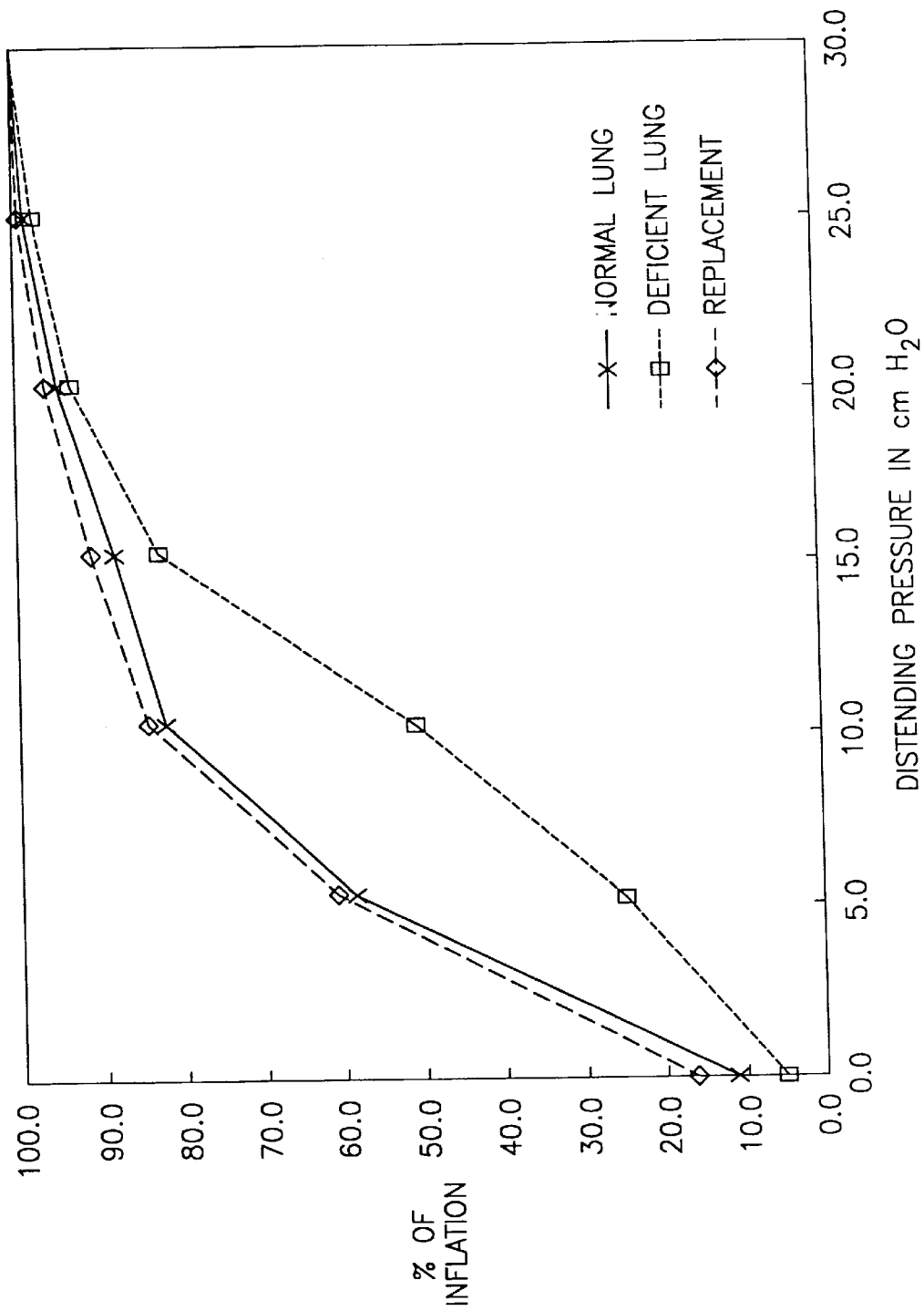

FIG. 2 displays the deflation curve of a lung excised from a mature rat.

[FIG. 2]

Curve 1: (X—X) depicts the decreasing volume of gas in the inflated lung as the distending pressure decreases from 30 cm $H_2O$ to 0 in the control status before manipulation.

Curve 2: (□—□) depicts the lower volume of gas at every distending pressure during deflation after the lung surfactant has been washed out by 20 consecutive lavages with 20–40 ml/kg body weight each.

Curve 3: (◊—◊) shows the deflation volumes restored to control values following instillation of the composition of the invention (in the dose of 100 mg/kg body weight) into the saline lavaged, surfactant deficient lung.

FIG. 1 demonstrates that instillation of the composition of the invention restores the integral of the deflation volumes to greater than 75% predeficiency levels at pressures of 5–20 cm $H_2O$.

5. DETAILED DESCRIPTION OF THE PREFERRED EMBODIMENTS OF THE INVENTION

The present invention is directed to the composition of matter and the method of making an organic extract of mammalian lung surfactant comprising protein, lipids, and water which maintains the biophysical properties and physiological properties of the extract at low total protein concentrations. In particular, the present invention relates to the composition and method of making and using a composition of matter that maintains at low total protein concentrations the biophysical and physiological characteristics of natural surfactant, including the rapid and spontaneous adsorption of dilute suspensions to an air-liquid interface; the generation of low surface tension (<2.1 mN/m) at a surface area compression of 50% by the pulsating bubble method of Enhorning; and the restoration to greater than 75% of normal the pressure-volume relationship of a surfactant deficient lung as decided by the method of Bermel. This invention is also directed to the therapeutic uses of the new material.

The composition of this invention can (1) reverse the collapse of alveoli, (2) stabilize alveoli which are progressing to collapse, (3) improve ventilation (thereby improving patient oxygenation and respiratory acidosis), (4) diminish the need for supplemental oxygen (which is toxic to the lung) and (5) lower the pressure assistance required to maintain breathing (which lowers the lung damage potential from barotrauma of mechanical ventilation).

In a preferred embodiment of the invention directed at extending the biophysical properties and physiologic activity at low total lipid concentrations, the saline lavage of a mammalian lung is extracted in a chloroform:methanol mixture and exogenous disaturated phospholipid is added to the extraction in an amount which increases the total phospholipid concentration by 25%. This new surfactant material can be used therapeutically in the same dosage, mg/kg body weight of total phospholipid, as the organic extract alone without loss of biophysical, physiologic or therapeutic activity.

In an embodiment of the invention directed at increasing the amount of therapeutic material able to be obtained from animal lung, an organic extract surfactant with added exogenous phospholipid will reduce production costs. Production costs will decrease because only a portion of the total therapeutic material must be recovered and extracted from animal lungs; the remaining portion is synthetic, defined material.

Another advantage of having an organic extract surfactant with added exogenous phospholipid results from improving the resistance of material to inhibition or inactivation by cell wall phospholipids. Inhibition or inactivation by cell wall phospholipids released by cellular destruction is less likely in vivo because the effect of such inhibition depends on the relative amounts of phosphatidylcholine (PC) to other phospholipids. Cell wall phospholipids will produce a smaller decrease in physiologic activity when the ratio of phosphatatidlycholine is high in relation to other phospholipids. The augmented extract of surface active material starts with a higher proportion of PC than does the unmodified extract of surface active material. Accordingly, the invention is less susceptible to inactivation by cell wall phospholipids.

In a more preferred embodiment of the invention, the exogenous disaturated phospholipid is added to the organic phase of the extraction.

In a more preferred embodiment of the invention, the exogenous disaturated phospholipid is dipalmatoylphosphatidylcholine (DPPC).

In an embodiment of the invention directed toward eliminating toxic solvents, the mechanical agitation is combined with at 90–99° C. while blowing nitrogen gas into the evaporation flask followed by 1–3 thermal agitations at 100–110° C. This method results in a suspended material that has low residual levels of toxic solvents (chloroform<10 parts per million and methanol<200 parts per million) with the desired biophysical properties and physiological activity.

In an embodiment of the invention directed at preparing the invention for use as a pharmaceutical product, the methodology of using terminal heat sterilization at 121–135° C. for 15–45 minutes after the suspension has been placed into a vial, capped and sealed has been determined to have no significant effect on biophysical properties or physiological activity. Terminal heat sterilization provides assurance that infectious agents will be inactivated and that the material is sterile before it is instilled into recipients.

5.1. Chemical Composition.

The organic extract of surface active material obtained from the lungs of mammals preferably comprises lipids, protein and water. Table I shows the contents of a preferred embodiment of the invention (in percent by weight) of total phospholipids, free fatty acids, cholesterol, and protein. Table I also shows the contents of a preferred embodiment of the invention (in percent by weight) of phospholipid constituents, and the content (in percent by weight) of phosphatidylcholine having two saturated fatty acid residues.

TABLE 1

Contents by Weight

| | |
|---|---|
| Total Phospholipid | 35 mg/ml |
| PC | 76–88% of PL |
| DPPC | 35–98% of PC |
| PE | 0.1–5% of PL |
| SPH | 0.1–5% of PL |
| PG | 4–10% of PL |
| PI | 0.1–5% of PL |
| LPC | <13% of PL |
| Protein* | 0.8–2.4% of PL |
| Cholesterol | 3.0–8.0% of PL |
| Surface tension | <2 mN/m @ 3–5 mg/l in 10 min on PBS at 37° C. |

*Protein consists of surfactant apoproteins B and C.

The analytical methods that may be used to measure the constituents of the organic extract of surface active material are described below.

5.1.1. Phospholipid Content

The phospholipid content of a preferred embodiment (in milligrams) was estimated by measuring its phosphorus content (in micromoles) by the method of Chen et al. and then multiplying the result by the average molecular weight of 750. (Chen PS, Toribara TY, Huber W: Microdetermination of phosphorous. Analyt Chem 1956; 28:1756–8.) In the Ames modification of the method of Chen method for measuring total phosphate, a sample containing organic phosphate is treated with magnesium nitrate solution and ashed over a flame. Any pyrophosphate formed during ashing is then hydrolyzed to phosphate by adding hydrochloric acid and heating in a boiling water bath. When an ammonium molybdate/ascorbic acid mixture is added, the phosphomolybdate complex is reduced by the ascorbic acid producing a blue color which can be read on a spectrophotometer at 820nm. This method is sensitive enough to determine 0.005 micromole of phosphate. A set of inorganic potassium phosphate monobasic standards ranging from 0 to 1.0 micromole of phosphate is run with each assay. The total phospholipid concentration (in mg/ml) in the sample is then calculated by dividing the result by the average formula weight for total surfactant phospholipids (0.750). (Ames BN, Dubin DT. J. Biol. Chem 1960; 235:769.)

The chemical composition of the phospholipid included in the preferred embodiment was analyzed as follows: phospholipid constituents were separated by one-dimensional thin-layer chromatography using a 0.25 mm thick, 20 cm long thin layer silica gel 60 (manufactured by Whatman) and the solvent system of Touchstone et al. (Touchstone JC, Chen JC, Beaver KM: Improved separation of phospholipids in thin layer chromatography. Lipids, 1980; 15:61–2.) Individual phospholipids were visualized with Rhodamine 6G, quantitatively extracted from the matrix, and concentration measured by the procedure described above for phosphorous content.

The content of phosphatidylcholine having two saturated fatty acid residues has been measured in the past using the method of Mason et al. (Mason RJ, Nellenbogen J, Clements JA: Isolation of disaturated phosphatidylcholine with osmium tetroxide. J Lipid Res 1976; 17:281–4.) However, attempts to validate that method revealed it to be nonspecific. Therefore, the disaturated PC content has been estimated from quantitative measurements of each of the fatty acids, as described by Yu et al. (Yu S, Harding PGR, Smith N, Possmayer F: Bovine pulmonary surfactant: chemical composition and physical properties. Lipids, 1983; 18:522–9.) Phosphatidylcholine is hydrolyzed using phospholipase $A_2$. Methyl esters of the free fatty acids are identified by high pressure gas liquid chromatography using known amounts of heptadecanoate as an internal standard.

Phospholipids are separated into their classes by thin layer chromatography utilizing the Touchstone solvent system of chloroform:methanol:isopropanol:triethylamine:water (36:10.8:30:30:8.4) as the mobile phase and a silica gel plate that has been pre-washed in the Touchstone solvent system and heat activated as the stationary phase. Following chromatography, the silica gel plate is dried, sprayed with Rhodamine 6G and visualized under UV light. The phospholipid spot of interest in the sample is identified by comparison to a set of phospholipid standards of the same type and known concentration also run on the plate. The scraped spots are then extracted by means of the Bligh and Dyer technique and assayed quantitatively for phosphate content by the Ames method.

5.1.2. Protein Content

The protein content was measured according to the method described by Lowry et al. (Lowry OH, Rosebrough NJ, Farr AL, et al.: Protein measurement with the folin phenol reagent. J Biol Chem 1951, 193:266–75), as modified for materials having high lipid content described by Petersen et al. (Peterson G. A simplification of the protein assay method of Lowry et al. which is more generally applicable. Analyt Biochem 1977; 83:346–56.) The protein assay is based on Peterson's modification of the micro-Lowry method for quantitation of soluble proteins. It utilizes sodium dodecyl sulfate (SDS) to facilitate the dissolution of relatively insoluble lipoproteins. The SDS does not interfere with the assay and in the presence of sodium hydroxide permits the immediate solubilization of proteins, leaving the lipids transparent and non-interfering. An alkaline cupric tartrate reagent complexes with the peptide bonds and forms a purple-blue color when phenol reagent is added. Absorbance is read on a spectrophotometer at 660nm and protein concentration is calculated by linear regression. A set of albumin standards ranging from 0 to 50 micrograms of protein is run with each assay.

5.1.3. Cholesterol Content

Total cholesterol content was measured by the method of Ferro et al. (Ferro, P. V., and A. B. Hamm, 1960, Rapid determination of total and free cholesterol in serum. Am. J. Clin. Path. 33:545.) The cholesterol assay utilizes a reagent containing glacial acetic, concentrated sulfuric and phosphoric acids, plus acetic anhydride to achieve development of color in the Liebermann-Burchard reaction. A standard curve ranging 0 to 4.0 mg/ml cholesterol is run with each assay. When color development is complete, absorbance is read at 625nm and the cholesterol concentration of the sample in mg/ml is calculated.

5.2. Biophysical Properties.

For a material to have optimal lung surfactant activity it must adsorb in seconds to an air-liquid interface and lower the surface tension at the interface in a manner similar to a detergent. The material must also lower surface tension to near 0 during surface compressions of less than 50% of the maximum area which is the greatest lung alveolar area change between total lung capacity at full inspiration and residual volume and the end of expiration.

These properties can be measured in vitro using either (1) a Wilhelmy balance, (2) an Enhorning pulsating bubble surfactometer, or (3) the captive bubble technique of Schursch.

A Wilhelmy Balance records the surface tension exerted on a platinum foil which is suspended from a force transducer into the surface while a movable barrier cyclically compresses or expands the surface of a liquid in a trough. Meaningful measurements require specification of liquid, temperature, maximum and minimum area, cycling rate, cycle of measurement and concentration of test material in the subphase or on the surface. (Tabak SA, Notter RH. A modified technique for dynamic surface pressure and relaxation measurements at the air water interface. Rev Sci Instrum 1977; 48:1196–1201.)

The pulsating bubble surfactometer (Electronetics, Amherst, N.Y.) measures the pressure across a spherical air-liquid interface at 37° C. which is cycling 140 times per minute with a 50% change is surface area during a cycle. A microprocessor calculates the surface tension using the La Place equation for spheres:

$$\Delta P = \frac{2\gamma}{R}$$

where AP is the pressure difference across the surface, $\gamma$ is the surface tension in mN/m, and R is the radius of the spherical bubble.

A disposable chamber is filled with 20 $\mu L$ of test solution and set upon a piston surrounded by a water bath. A bubble is created by drawing air through a capillary chimney when the piston is moved from its thrust to its withdrawal position. An equilibrium surface tension is calculated when the pressure equilibrates. Cycling of the piston is then initiated and pressure and calculated surface tension continually recorded. Measurements are continued until minimum surface tension decreases to <1 mN/m, or 10 minutes of cycling has elapsed. (Enhorning GE, Pulsating Bubble Technique for Evaluating Pulmonary Surfactant, J. Appl. Physiol. 1977, 43, 198–203.)

The captive bubble technique measures the change in size of a bubble created in a closed vessel containing test material following the cyclical application of pressure driven compression and expansion of the bubble volume. The bubble size is computed from external imaging. Surface tension is calculated from bubble shape, applied compression pressure, and bubble surface area. (Schurch A, Bachofen H, Goerke J, Possmayer F. A captive bubble method reproduces the in situ behavior of lung surfactant monolayers. J Appl Physiol 1989; 67:2389–96.)

5.2.1. Adsorption Properties at a Gas-Liquid Interface

The rate of the adsorption of suspended material of this invention to a gas-liquid interface of a spherical surface of a bubble of defined radius was estimated according to the method of Enhorning and Holm and colleagues. (Enhorning GE, Pulsating Bubble Technique for Evaluating Pulmonary Surfactant J. Appl. Physiol. 1977, 43, 198–203, 1977; Holm BA, Venkitaraman AR, Enhoming G, Notter RH. Biophysical inhibition of synthetic lung surfactants. Chem Phys Lipids 1990; 52:243–250.)

Adsorption is measured at the start of a study. A bubble is formed manually and the size held constant. The trace recording is started just before the bubble is created. The bottom trace, pressure, and the top trace, surface tension will stop changing and come to a steady state at equilibrium surface tension. This means that the surfactant has adsorbed onto the surface. The time between bubble creation and reaching the equilibrium surface tension is the adsorption time.

A suspension containing 1–5 milligrams of the preferred embodiment of this invention per milliliter of physiological saline was prepared at 37±2° C. Surface tension of the suspension is measured over time until an equilibrium surface tension is attained. The invention adsorbed to a surface and decreased the surface tension of physiological saline from its initial value of 45 mN/m to a constant value of 22–26 mN/m within 10 seconds.

5.2.2. Surface Tension Reducing Capacity

The preferred embodiment of this invention was assessed for surface tension reducing characteristics by the pulsating bubble method of Enhorning. Enhorning GE, Pulsating Bubble Technique for Evaluating Pulmonary Surfactant, Journal of Applied Physiology 43, 198, 1977). The bubble surfactometer consists of a 20 $\mu l$ sample chamber filled with a test material in an aqueous phase which is maintained at 37° C. The sample chamber is connected to the atmosphere through a small chimney. A pressure transducer constantly measures the pressure of the test material. By displacement of the head of a small piston, the volume inside the sample chamber is increased by influx of atmospheric gas through the chimney to form a bubble whose maximum radius is fixed. Cycling of piston position produces an oscillating bubble whose maximum and minimum size is determined by piston displacement. The surface tension of the bubble is calculated by a microprocessor at maximum and minimum radius from the LaPlace equation and the difference between atmospheric and test chamber pressure.

An air bubble with a surface area of 3.6 $mm^2$ was formed in a 25 microliter sample of the suspended surface active material at a total phospholipid concentration of 1–5 mg/ml and a temperature of 37±2° C. The bubble size was then oscillated between its initial value and a reduced size with a surface area of 1.8 $mm^2$ at a rate of 20 cycles/minute. The composition of the invention lowered the surface tension to less than 2.1 mN/m within 1–100 cycles.

5.2.3. Restoration of Lung Pressure-Volume Mechanics

As adapted from the method of Bermel, pressure/volume curves are performed on the excised lung of a healthy adult rat. (Bermel MS, McBride JY, Notter RH: Lavaged excised rat lungs as a model of surfactant deficiency. Lung 1984; 162:99–113.)

After the rat is sacrificed, its lung is harvested by dissection from the thoracic cavity and maintained in 0.9% saline. Trapped gas is removed from the lung by vacuum then it is connected to a system consisting of a closed volume of gas and a reservoir filled with indicating fluid contiguous with a buret. The system is interfaced with a strain gauge pressure transducer (which has been calibrated against a water manometer) and a chart recorder.

Pressure/volume curves are obtained by raising the buret to inflate the lung to total capacity (30 cm water pressure) then deflating the lung by lowering the buret in stepwise increments. Readings of gas volume displacement (in ml) within the lung are made every 5 cm of water pressure and are recorded on the chart recorder. At static conditions, measured volume is corrected for gas compression.

Pressure/volume curves are performed on the lung under three conditions: (1) the normal state (post excision) which tests the activity of endogenous surfactant and serves as the positive control, (2) the surfactant deficient state after the lung has been thoroughly lavaged with 0.9% saline, (this removes endogenous surfactant and serves as the negative control) and (3) after the lung has been instilled with the test material in effort to restore the surfactant sufficient (normal) state.

Lungs from adult rats were excised, air in the lungs was removed by vacuum, and the lungs were rapidly inflated to a trans-pulmonary pressure of 30 cm water. A positive control pressure-volume curve was then obtained by deflating the lung to a trans-pulmonary pressure of 0 cm water while continuously monitoring both lung volume and transpulmonary pressure. The lungs were then made surfactant deficient by repeated lavage with 0.15M NaCl. Surfactant deficiency is achieved when the sums of volumes remaining in the lung at 15, 10 and 5 cm $H_2O$ on the deflation curve are $\leq 70\%$ of the values measured on the normal lung before the endogenous surfactant was removed by saline washing. The surfactant deficient lungs were used to generate a negative control pressure-volume curve. A 2.5 ml sample of the preferred embodiment of this invention was then instilled into the surfactant-deficient lung, and a third pressure-volume curve was defined as described above to determine the ability of the material to improve pressure-volume characteristics toward the level of the positive control.

The relationship described by FIG. 2 is the percent of the measures the ability of the composition of the invention to improve the pressure-volume mechanics of a surfactant-deficient lung was assayed by the method of Bermel, as described above.

The preferred embodiment of the invention restored greater than 75% of the lost lung volume of the surfactant deficient excised rat lung compared to the positive control value when instilled at concentrations of 2–10 mg/ml.

5.3. Preparation of The Extracted Surface Active Material.

The following subsections provide detailed descriptions of preferred embodiments of the present invention. These descriptions are intended for descriptive purposes only, in no way limiting the scope of the invention.

5.3.1. Collection of Surface Active Material

The object of this aspect of the invention is to obtain mammalian lungs as a source for surface active material. The lung preferably may be obtained from cattle, pigs, sheep, horses, dogs, cats, or rabbits of any age. The surface active material may be isolated from the lung in situ or the lungs with trachea intact may be removed from the mammal prior to isolation of surface active material. In a preferred embodiment of the invention, lungs with trachea intact are removed from freshly killed newborn calves and placed at 0–10° C. for less than 16 hours before processing.

Surface active material can be isolated by rinsing (lavaging) the air spaces of the lung.

In a preferred embodiment of this invention, surface active material is removed from the airways of mammalian lungs by the process of brochoalveolar lavage. An endotracheal tube may be secured in the trachea of the isolated lung and a volume of aqueous solution, such as physiological saline, may be instilled and allowed to fill the lung airway by gravity. The bronchoalveolar lavage may then be removed and collected from the lung airway by vacuum or gravitational drainage.

5.3.1.1. Concentration of Isolated Surface Active Material

The bronchoalveolar lavage is combined with an aqueous solution to suspend the natural surfactant. In a preferred embodiment, the fluid collected by bronchoalveolar lavage is centrifuged at a speed of $\geq 100$ g for $\geq 1$ minute to collect a concentrated sediment of surface active material. The sediment of surface active material preferably is then brought to desired volume by addition of an aqueous solution, such as physiological saline.

5.3.2. Extraction and Isolation of Surface Active Material

Extraction of surface active material from the aqueous suspension may be carried out using various organic solvents, including, but not limited to, chloroform, benzene, and mixtures of chloroform and methanol, ether and ethanol, and hexane and ethanol.

In a preferred embodiment, a mixture of chloroform and methanol is prepared using 2 volumes of chloroform to one volume of methanol. Three volumes of the chloroform-methanol mixture preferably is added to 0.8 volumes of the aqueous suspension of surface active material. A subsequent additional volume of chloroform preferably is added, and a final 1 volume of water preferably completes the extraction protocol. The resulting mixture preferably is allowed to separate into multiple phases at 0–25° C., as described by Bligh and Dyer. (Bligh EG and Dyer WJ, A Rapid Method of Total Lipid Extraction and Purification, Canadian Journal of Biochemistry and Physiology 37, 911, 1959.)

According to the method of Bligh and Dyer, one part aqueous suspension of sample is combined with 3.75 parts of a mixture of chloroform:methanol (1:2) such that a miscible system is formed. Dilution with 1.25 parts of chloroform followed by 1.25 parts of water separates the mixture into two layers, the chloroform layer containing all the lipids and a methanolic layer containing all the non-lipids. A purified lipid extract is obtained merely by isolating the chloroform layer.

In this preferred embodiment, the extraction mixture separates into three distinct phases. The bottom phase is composed primarily of chloroform and has in solution those components of surface active material that are soluble in organic solvent and insoluble in aqueous solutions. The top phase contains a methanol-water solution plus water soluble materials from the surface active material. The middle phase, or interphase, contains material from the aqueous suspension of surface active material that is insoluble in either the chloroform or the methanol:water phase such as denatured and hydophilic proteins. The bottom phase preferably is carefully collected to insure that it is not contaminated by insoluble material from the interphase or by materials in the water:methanol phase. The chloroform layer contains dissolved surface active material and a small amount of methanol.

5.4. Augmentation of Extracted Surface Active Material.

The extracted surface active material may be augmented in the composition of the present invention with additional disaturated phospholipids such that the ratio of phospholipid to protein increases from 50:1 to the range of 55:1 to 70:1. The total phospholipid of the resulting composition preferably is 10–40% greater than that of the extracted surface active material prior to augmentation.

The disaturated phospholipids to be used for augmentation may contain a three carbon glycerol phosphate backbone to which fatty acids containing no double bonds are esterified in the Sn-1 and Sn-2 positions. Further, these lipids may be phosphatidylesters wherein the phosophatidic acid molecule is esterified to the hydroxyl groups of ethanolamine, choline, or serine. The fatty acid moieties of these glycerophosphatides, may include one or more of palmitic acid, myristic acid, margaric acid, and stearic acid.

In a preferred embodiment, the disaturated phospholipid is added to the surface active material in the organic phase of the extraction. In a further preferred embodiment, DPPC is added to the surface active material in the organic phase of the extraction.

In a preferred embodiment, the extraction is a Bligh & Dyer extraction.

5.5. Removal of Organic Solvent From Augmented Surface Active Material

Organic solvent is removed from the extract of surface active material. This can be done by one or more of the following: distillation, lyophylization, and vacuum evaporation.

In a preferred embodiment, the extracted surface active material is placed in a round-bottomed flask and rotated slowly (<300 revolutions per minute), while heated at a temperature between the gel to liquid phase transition temperature for DPPC and the boiling point of water.

In a further preferred embodiment, the round bottom flask is rotated at 150 revolutions per minute at 99° C.

In a further preferred embodiment, the flask containing the extract of surface active material is placed under a vacuum to facilitate evaporation of organic solvent. The evacuation of the organic solvent vapors is carried out in a manner, such as distillation, that facilitates the separation of the organic solvent from the surface active extract.

In each preferred embodiment, the evacuation is continued until the surface active material is dried onto the surface of the flask.

5.6. Resuspension of Augmented Surface Active Material in Aqueous Solution

In an embodiment of the invention, the surface active material which has been separated from the organic solvent is resuspended in an aqueous solution. Resuspension may be accomplished by spontaneous suspension over time or physical energy from (1) mechanical vortex mixing, (2) ultrasonic vibrations, (3) microwave agitations, or (4) high temperature.

In a preferred embodiment of the present invention, a sterile 0.9% saline solution is added to the dried surface active material and heated as the flask is rotated.

In a further preferred embodiment, the flask is heated at 42–99° C. for 10–60 minutes.

In a further preferred embodiment, the flask is rotated slowly at less than 300 revolutions per minute.

In a further preferred embodiment, the resuspension is accomplished by thermal agitation at a temperature above the boiling point of water.

In a further preferred embodiment, the vessel containing the resuspension is subsequently heated to greater than 100° C. under a pressure of 1–5 atmospheres to complete the resuspension and the chloroform evaporation, and then gradually cooled. This process of heating resuspension to greater than 100° C. and cooling may be repeated 1 to 3 times.

After cooling, the suspension of surface active material may be stored at 0–10° C. for up to 96 hours.

5.6.1. Sterilization of the Resuspension of Augmented Surface Active Material The suspension of surface active material may be sterilized for use as a pharmaceutical product. Sterilization may be achieved by ultrafiltration, sterile resuspension, gamma radiation, or terminal heating. In a preferred embodiment, the suspension is sterilized by applying heat at a pressure of greater than one atmosphere for up to one hour. In a further preferred embodiment, the suspended surface active material is placed in a sealed glass vial and sterilized by applying heat at a temperature of 121–135° C. at greater than 1 atmosphere pressure for 10–60 minutes.

5.7. Pharmaceutical Product.

The preferred embodiment of the invention may be used as a pharmaceutical product. The components of the preferred embodiment are natural and non-toxic. The preferred embodiment can be instilled repeatedly in the lungs of normal animals without toxic effects on the lung or other organs. The proteins do not create a sensitivity reaction when injected into guinea pigs. In addition, the product withstands steam heat sterilization so it can be prepared free from microbial contamination. The material can improve lung functions when instilled in mammals with respiratory deficiency due to congenital, infectious, toxic, immune, inflammatory, or traumatic lung disease.

5.8. Administration of Augmented Surface Active Material

Deficiency and/or inactivation of lung surfactant contributes to the lung pathology that results in the inability to ventilate adequately. In the treatment of respiratory disease, a sterile pharmaceutical product made from the preferred embodiment of the invention is instilled into the lumen of the airway to prevent or treat respiratory disease that is wholly or partly caused by surfactant dysfunction or deficiency. Various methods of instillation have been used including, (1) single bolus injection, (2) multiple, smaller bolus injection, (3) injection as a fine spray during inspiration while on mechanical ventilation, or (4) administration as an aerosol. Appropriate doses range from 15 to 150 mg/kg body weight. Treatment can be repeated as needed if inadequate gas exchange, decreased lung compliance, or medical diagnosis indicate continuing or recurrent surfactant deficiency or dysfunction. By administering the surface active material as an aerosol, the effective dose can be decreased.

5.9. Therapeutic Uses.

5.9.1. Prophylaxis for Premature Infants at Birth

Large, prospective clinical trials have documented that instillation of surface active material at birth, rather than waiting to determine if an infant is going to develop RDS, reduces death and severe lung disease for infants born >7 weeks before term. (Kendig JW, Notter RH, Cox C, et al.: A comparison of surfactant as immediate prophylaxis and as rescue therapy in newborns of less than 30 weeks gestation. N Engl J Med 1991; 324:865–71; Kattwinkel J, Bloom BT, Delmore P, et al.: Prophylactic Administration of Calf Lung Surfactant Extract is more effective than early treatment of respiratory distress syndrome in neonates 29 through 32 weeks gestation. Pediatrics 1993; 92:90–8.) Infants born between extrauterine viability, approximately 22 weeks of gestation, and full term of pregnancy, approximately 38 weeks of gestation, have a risk of inadequate lung surfactant. Administration of the composition of the invention at birth can lower the incidence and severity of that disease in these infants.

5.9.2. Treatment of Patients with Respiratory Distress Syndromes

Patients who have RDS have non-compliant lungs, atelectasis (collapsed, non-aerated alveoli) scattered throughout the lung, and mismatching of ventilation and blood flow within the lung, thereby requiring added oxygen in the inspired air to maintain sufficient oxygen in the blood. These patients have difficulty breathing ranging from labored breathing to requiring mechanical assistance to survive. The chest radiograph shows a classic "hazy" pattern in the lung fields from atelectasis, decreased lung aeration and accumulation of excess fluid in the lungs. Deficiency and/or inactivation of lung surfactant produces that atelectasis and prevents their easy re-aeration with increased inspiration of gas. The administration of the composition of the invention improves ventilation and decreases the amount of supplemental oxygen required by patients who have RDS.

5.9.3. Treatment of Patients with Acute Respiratory Failure

Patients who have acute respiratory failure, hypoxia and hypercapnia from acute lung disease, and who require ventilatory assistance may have inactivation or deficiency of lung surfactant as one component of their pathophysiology. The severity of the respiratory failure from acute lung disease will be diminished and the quantitative requirements for mechanically assisted ventilation and oxygen enrichment of inspired gas lowered by therapy with exogenous lung surfactant extract. Patients with physiologic indications of respiratory failure and evidence of acute lung disease as the cause by clinical examination, diagnostic imaging and laboratory testing can be improved by therapy with the composition of the invention.

5.9.4. Treatment of Patients with Lung Inhalation Injuries

Patients who suffered from respiratory disease and decreased lung function following inhalation of a gas whose temperature is too hot or too cold, or which contains toxic gases or particulates, or which contains insufficient oxygen to meet a patients needs, have a lung injury syndrome. Experimental evidence shown that an extract of surface active material instilled into the airspace after lung injury from 5 minutes of smoke inhalation in dogs can ameliorate the dysfunction of the lungs. Patients who have physiologic and clinical evidence of inhalation injury to the lung will improve with treatment with the composition of the invention.

5.9.5. Prophylaxis of Patients at Risk of Acute Lung Disease

Some patients undertake therapies for severe diseases which have a significant risk for lung diseases at least partially caused by inactivation of lung surfactant and/or injury to surfactant producing calls. Ventilation without adequate surfactant accelerates further damage to a lung. Prophylaxis of patients with exogenous surfactant extract after extensive cardiopulmonary bypass, bone marrow transportation, lung transplantation, some cancer chemotherapies and some gene therapies will be indicated based on the estimated risk of the therapy for that patient. It is more effective to use therapy with the composition of the invention as part of the treatment for their primary disease rather than delaying surfactant replacement therapy until the pulmonary complications have advanced.

5.9.6. Therapy for Obstructive Syndrome of Small Airways

Patients whose small airway disease is due wholly or in part to closure of small airways in the periphery of the lung from absence or inactivation of lung surfactant merit treatment with an extract of surface active material. These patients display symptoms of respiratory difficulty, clinical and lung image evidence of small airway disease characterized by air trapping and lung hyperexpansion. Clinical and physiologic evaluation reveals decreased ventilation. Treatment with the composition of the invention will improve ventilation, decrease small airway obstruction, and diminish the respiratory difficulty.

6. EXAMPLES

6.1. Recovery of Surface Active Material from Bovine Lungs by Lavage

The following procedure was used to prepare a preferred embodiment of the composition of this invention. Polypropylene tubes were secured into the tracheas of 12 pairs of excised bovine lungs, and the lungs were filled to capacity with 0.15 M sodium chloride. The saline solution was withdrawn from the lungs by applying suction to the endotracheal tube and approximately one liter of bronchoalveolar lavage fluid was collected from each. This rinsing procedure was repeated for each pair of lungs. The recovered lavage material was pooled and then poured into 800 ml centrifuge bottles and spun at 14,000×g for 30 minutes at 5° C.

6.2. Extraction of Surface Active Material

The sediment was resuspended in 100 ml of 0.15 M NaCl and stirred gently. To this suspension, 376 ml of a 2:1 (vol:vol) mixture of chloroform:methanol was added and stirred gently. Next, 126 ml of chloroform and 126 ml water were added; the mixture was stirred gently for one minute and allowed to stand at 25° C. until a two phase separation occurred. The chloroform phase was removed, and 130 ml of material was placed in a round bottom flask. The flask containing the chloroform material was attached to a rotoevaporator distillation device, and the flask was rotated at 50 rpm at 62° C. under vacuum for 30 minutes with a stream of nitrogen flowing over the chloroform surface. This process resulted in a dry residue of surface active material coating the walls of the flask.

6.3. Addition of Exogenous Phospholipid to the Extracted Surface Active Material in Organic Solvent Surface active extract was augmented with exogenous phospholipid as follows:

1. To 16 grams of phospholipids of lung lavage extract dissolved in chloroform, 4 grams of dipalmitoylphosphatidylcholine was added and mixed gently before the chloroform was removed.
2. The flasks containing the DPPC-augmented chloroform material was attached to a rotoevaporator distillation device, and the flasks were rotated at 50 rpm at 62° C. under vacuum for 30 minutes with a stream of nitrogen flowing over the chloroform surface.

This process resulted in a dry residue of surface active material coating the walls of the flasks.

6.4. Resuspension of Extracted Surface Active Material With or Without Exogenous Phospholipids.

140 ml of sterile 0.15 M NaCl was added to the dry residue of surface active material with or without exogenous disaturated phospholipid. The flask was then rotated at 50 rpm at 99° C. for 30 minutes while a stream of nitrogen was passed over the surface of the saline solution. This suspension was then autoclaved three times for 20 minutes each at 120° C. The suspension was then placed at 4° C. for 12 hours. The material was sealed and capped for use as a pharmaceutical product.

6.5. Addition of Exogenous Phospholipid to the Extracted Surface Active Material in Aqueous Medium.

Resuspended surface active extract was augmented with exogenous phospholipid as follows:

1. After the addition of 140 ml of 0.15 M NaCl to the dry residue as described in 6.3, 1.0 grams of DPPC was added to the surface active material.
2. The flask was rotated at 50 rpm at 99° C. for 30 minutes while a stream of nitrogen was passed over the surface of the saline solution.
3. The suspension was autoclaved three times for 20 minutes at 120° C., and then placed at 4° C. for 12 hours.

The material was sealed and capped for use as a pharmaceutical product.

6.6. Biophysical Assays.

The biophysical activity of surface active material was assayed as follows:

1. The surface active material suspended in saline was diluted with normal saline to a phospholipid concentration of 2–10 mg/ml.
2. Twenty microliters of the diluted surface active material were added by capillary tube to a sample chamber prepared for a pulsating bubble surfactometer (Electronetics Corp., Amherst, N.Y.).
3. The sample was placed in the surfactometer, an air bubble was formed within the sample, and the bubble was pulsated at 20 cycles per minute at a 50% surface area compression of the bubble.
4. Surface tension readings at minimum bubble radius were recorded for 10 minutes or until a surface tension <2.1 mN/m was achieved.

6.7. Physiological Assays.
6.7.1. Physiological Assays in Excised Lungs The physiological activity of surface active material were assayed as follows:

1. Lungs from adult rats were excised, degassed by vacuum, and rapidly inflated to a trans-pulmonary pressure of 30 cm water.
2. A positive control pressure-volume curve was defined by deflating the lung to a trans-pulmonary pressure of 0 cm water while continuously monitoring both lung volume and trans-pulmonary pressure.
3. The lungs were made surfactant deficient by repeated lavage with 0.15 M NaCl. A negative control pressure-volume curve was defined by inflating the lungs to a trans-pulmonary pressure of 30 cm water and then deflating the lung to a trans-pulmonary pressure of 0 cm water.
4. 50–100 mg/kg body weight of surface active material was instilled into the surfactant-deficient lung in 2.5 ml physiological saline, and a third pressure-volume curve was defined by inflation to 30 cm water pressure and then deflating the lung to a trans-pulmonary pressure of 0 cm water pressure.

The studies on excised rat lungs demonstrated that the composition of the invention restores greater than 75% of the lost volume to the surfactant deficient lung. See FIG. 2.

6.7.2. Physiological assays in premature mammals

A fetus is delivered by surgical hysterotomy before maturation of lung surfactant, 125±5 of 150 days in sheep, 27±1 of 30 days in rabbits, 125±2 of 180 days in baboons. Before the first breath a single bolus of 3 ml/kg (100 mg/kg) body weight of the preferred embodiment of the invention was instilled into the trachea of a sheep fetus. The immature animal was mechanically ventilated, with 100% oxygen. Prolonged survival of the animals with fully oxygenated of arterial blood (≧95% saturation) was documented by an 8 hour experiment.

6.8. Administration of Augmented Surface Active.
6.8.1. General

Lung surfactant replacement preparations derived from mammalian lung surfactant extracts are suspended in aqueous solutions whose osmolality approximates that of mammalian plasma. These solutions also have a pH in the range of 4.0–8.0 which parallels that of NaCl solutions.

The sterile suspension is packaged in a vial that is stored in a refrigerated environment of 2–8° C. These vials are single use containers which are entered using a needle and syringe to withdraw the material.

The lung surfactant replacement material acts in the lumen of the lung at the interface of gas and the thin liquid film that lies on the surface of the epithelial cells that line the lung called the alveolar lining layer. The suspension is instilled directly into the trachea of the lung where it is carried by instillation momentum and gravity to the peripheral areas of the lung. Alternatively, the surfactant material is delivered into the lumen of the air space by aerosolizing the suspension so that it is carried into the lung lumen by inspired air.

6.8.2. Preparing a Dose of the Augmented Surface Active Material (a) The usual dose ranges from 10–150 mg phospholipid per kilogram body weight. The optimal dose in a specific situation depends upon the method of administration, the pathologic condition targeted, and the therapeutic strategy—whether the indication is to prevent the onset of a pathology, limit the progression of the pathologic process or reverse the respiratory failure that has already occurred.

(b) One or more vials are removed from the refrigerated storage place and the settled material in the dependent areas of the vial is resuspended by a gentle rocking motion. Care is taken to avoid over-agitation which will promote foaming. The suspension does not need to be warmed. The surfactant extract can be 0–37° C. when it is instilled because the airway will warm it to body temperature when it is instilled.

(c) Using sterile technique, the calculated dose is withdrawn by puncturing the stopper(s) of the vial(s) with a hypodermic needle attached to a sterile plastic or glass syringe and aspirating the surfactant extract suspension into the syringe.

(d) The material is retained in the syringe(s) using sterile precautions until the actual installation.

6.8.3. Preparing a Recipient for a Dose of the Augmented Surface Active Material For instillation, the recipient is intubated. An endotracheal tube is inserted or, if it is already in place, its position in the trachea is verified. If the administration uses direct instillation through a catheter, tracheal puncture, or bronchoscopy the recipient is positioned and anesthetized and/or sedated as necessary for patient comfort and safety during the technical procedure.

6.8.4. Administration of the Augmented Surface Active Material By Instillation (a) Prophylactic administration of the preferred embodiment of the invention at birth is delivered as a single bolus into the air space followed by positive pressure of gas which propels the normal lung liquid present before birth in fetuses and the surfactant extract suspension to the periphery of the lung and establishes lung aeration and ventilation.

(b) Administration by multiple boluses, followed by positive pressure of gas, uses the force of gravity and the positive airway pressure to propel the instilled suspension of surfactant active material to dependent and peripheral parts of the lung. Multiple boluses are used so that the patient's position can be changed between boluses to optimize peripheral distribution by gravity and to prevent harmful interruption of gas ventilation by the instillation of too large a bolus of the suspension liquid.

(c) Administration by spraying tiny amounts into the airspace during inspiration with positive pressure ventilation allows ventilation and gravity to move the surfactant extract to the periphery of the lung.

6.8.5. Administration of the Augmented Surface Active Material By Aerosol

The preferred imbodiment of the invention is administered by the creation of microdroplets by atomizers or aerosol generators. The aerodynamic radius of the microdroplet is adjusted between $10^{-7}$ meters (0.1 micrometer) and $10^{-4}$ meters (100 micrometers) by the microdroplet generator and/or delivery system to achieve the microdroplet size range desired for a particular pharmacologic use. When administered to the lung lumen by devices and systems that provide optimal deposition, lower doses, up to 95% lower, can be used in some indications than are needed if administration using an instillation technology is employed. The decrease in the dose needed is the result of more even distribution among the alveoli which is achieved by microdroplet administration methodologies than can be achieved with any instillation methodologies.

6.9. Use as a Pharmaceutical Agent.

6.9.1. Prophylaxis Treatment at Birth For Infants at High Risk For Respiratory Distress Syndrome (RDS)

Prospective clinical trials have shown that surfactant prophylaxis for infants born 32 weeks gestation or earlier lowers mortality and the incidence of chronic lung disease compared to infants whose surfactant therapy is delayed until the outset of disease. Therefore, infants at high risk for congenital deficiency of surfactant because of prematurity or inborn abnormalities of surfactant proteins are improved when the composition of the invention is instilled into the trachea at birth. The composition of the invention acts at the alveolar level to stabilize lung expansion and facilitates ventilation and gas exchange. Repeated doses may or may not be needed depending on the rate of induction of normal surfactant metabolism by the infant's own lungs. Need for retreatment is indicated by the onset of the signs and symptoms of respiratory failure, including (a) increasing supplemental oxygen requirements and (b) increasing requirements for higher inspiratory pressures on mechanical ventilators.

6.9.2. Treatment of Patients With Respiratory Failure From Respiratory Distress Syndromes (RDS)

The composition of the invention is instilled through the trachea into the lungs of patients who have respiratory failure due to respiratory distress syndromes.

6.9.3. Treatment of Patients With Respiratory Failure from Other Lung Diseases Patients who suffer respiratory failure are not able to maintain adequate oxygen uptake and carbon dioxide excretion without mechanical support of ventilation and mechanical stabilization of lung aeration and/or supplementation with additional oxygen in the inspired gas. In these patients, if lung surfactant deficiency or dysfunction is contributing to the respiratory failure, there will be radiologic evidence of collapse of some alveoli (atelectasis), decreased compliance of the lung, and/or hypoxemia by a low ratio of arterial to alveolar partial pressure of oxygen (a/A $pO_2$). Inactivation of alveolar lung surfactant and/or dysfunction of alveolar Type II cells leading to diminished lung surfactant secretion or secretion of defective lung surfactant would result in respiratory failure that would be treated by lung surfactant replacement. The composition of this invention can improve respiratory function in respiratory failure by restoring lung surfactant activity, and the composition of this invention resists inactivation by such diseases processes.

6.9.4. Treatment of Patients With Inhalation Injury to the Lung

The inhalation of gases hot enough or cold enough to burn lung tissue and/or gases that contain chemically active components that react with lung tissues or lung surfactant cause respiratory diseases. The aspiration or instillation of liquids (solutions or suspensions, with or without particulate matter), causes injury to lung tissue and diminishes the activity of lung surfactant. These injuries can be caused by reactive molecules dissolved or suspended in the liquid, the chemical action of the solvent on lung tissue or lung surfactant, or the obstruction of airways and/or physical injury to tissues and/or surfactant from particulates. These inhalation injuries will damage both extracellular lung surfactant and type II alveolar cells that control endogenous lung surfactant synthesis and secretion. The composition of this invention can improve respiratory function by restoring lung surfactant activity and by resisting inactivation by inhaled toxins and particulates.

6.9.5. Prophylaxis by Instillation of Lung Surfactant Into Patients at High Risk For Respiratory Disease Due to Lung Surfactant Inactivation or Injury to Type II Alveolar Cell Activity Some therapies for diseases are associated with a significant risk for respiratory complications. One component of the respiratory complication is the inactivation of lung surfactant and/or injury and abnormal function of the alveolar type II cell. Therapies such as surgery using heart-lung bypass, cancer chemotherapy, bone marrow transplantation, radiation therapy and, in the future, gene therapies using systemic strategies for inserting additional gene sequences in somatic cells or respiratory strategies for insertion of additional gene sequences into respiratory system cells directly are situations in which risk of respiratory complications will occur in certain patients.

In some circumstances, the optimal strategy may be to diminish the incidence and/or severity of respiratory complications from these therapies by instillation of exogenous lung surfactant before clinical evidence of respiratory signs or symptoms are present. The exogenous surfactant would provide the patient with an additional quantitative reserve of lung surfactant at the start of a therapy that might threaten the integrity of the normal lung surfactant system. The composition of the invention would resist inactivation by such processes.

6.9.6. Treatment of Obstructive Syndromes of Small Airways

Resistance to airflow in a lung diminishes from the trachea to the periphery because at each branching of the airway the cross-section area of the two daughter bronchi exceeds that of the parent bronchus. However, obstruction of the smallest conducting airways in expiration may prevent adequate exhalation and contribute to significant clinical disease of the respiratory tract. Although common wisdom has ascribed this obstruction to pathologic constriction of small airway smooth muscle, newer insights suggest that cellular swelling and inflammation may contribute to the obstruction. (Definition and Diagnosis, Guideline for the Diagnosis and Management of Asthma, Expert Panel Report, National Institute of Health, US Department of Health and Human Services, Publication No. 91–3042, 1991, pp. 1–13.) Further, recent research has suggested that patency of small airways, those 30–1000 microns in radius, may be dependent upon having adequate amounts of active lung surfactant. Inactivation of small airway lung surfactant (due to the same processes that promote inflammation) or inadequate amounts of small airway lung surfactant due to dysfunction of production or secretion could be treated by administration of an exogenous lung surfactant. The composition of the invention resists inactivation by these processes.

What is claimed is:

1. A composition of matter derived from the lavage of whole lungs comprising:
   (a) surface active material containing lipid, protein and water; and
   (b) further phospholipid;
such that (i) the composition adsorbs to a surface and decreases the surface tension of physiological saline to an equilibrium surface tension within 10 seconds; (ii) the minimum surface tension of the composition is less than 2.1 mN/m at a surface area compression of 50% by the pulsating bubble method of Enhorning at total lipid concentrations of less than 10 mg/ml of the compositions and (iii) the composition restores the pressure-volume mechanics of surface deficient lung by more than 75% of the lost lung volume in the excised lung test of Bermel.

2. The composition of claim 1 wherein the surface active material comprises by dry weight:
   (a) about 85–99% lipid; and
   (b) about 1–3% protein.

3. The composition of claim 2 wherein the lipid comprises about 85–98% phospholipid.

4. The composition of claim 2 wherein the lipid comprises between 0 and about 10% cholesterol.

5. A composition of matter derived from the lavage of whole lungs comprising:
   (a) surface active material containing lipid, protein and water; and
   (b) further phospholipid;
such that (i) the composition adsorbs to a surface and decreases the surface tension of physiological saline to an equilibrium surface tension within 10 seconds; (ii) the minimum surface tension of the composition is less than 2.1 mN/m at a surface area compression of 50% by the pulsating bubble method of Enhorning at total lipid concentrations of less than 5 mg/ml of the compositions and (iii) the composition restores the pressure-volume mechanics of surface deficient lung by more than 75% of the lost lung volume in the excised lung test of Bermel.

6. The composition of claim 5 wherein the surface active material comprises by dry weight:
   (a) about 85–99% lipid; and
   (b) about 1–3% protein.

7. The composition of claim 6 wherein the lipid comprises about 85–98% phospholipid.

8. The composition of claim 6 wherein the lipid comprises between 0 and about 10% cholesterol.

9. A composition of matter derived from the lavage of whole lungs comprising:
   (a) surface active material containing lipid, protein and water; and
   (b) further phospholipid,
such that (i) the composition adsorbs to a surface and decreases the surface tension of physiological saline to an equilibrium surface tension within 10 seconds: (ii) the minimum surface tension of the composition is less than 2.1 mN/m at a surface area compression of 50% by the pulsating bubble method of Enhorning at total lipid concentrations of less than 2 mg/ml of the composition; and (iii) the composition restores the pressure-volume mechanics of surface deficient lung by more than 75% of the lost lung volume in the excised lung test of Bermel.

10. The composition of claim 9 wherein the surface active material comprises by dry weight:
    (a) about 85–99% lipid; and
    (b) about 1–3% protein.

11. The composition of claim 10 wherein the lipid comprises about 85–98% phospholipid.

12. The composition of claim 10 wherein the lipid comprises between 0 and about 10% cholesterol.

13. The composition of claims 2, 6, or 10 wherein the further phospholipid comprises a disaturated phospholipid.

14. The composition of claim 13 wherein the further phospholipid comprises dipalmitoylphosphatidylcholine.

15. The composition of claim 3, 7, or 11 wherein the amount of further phospholipid comprises about 10–40% of the amount of phospholipid in the composition.

16. The composition of claim 2, 6, or 10 wherein the ratio of total phospholipid of the composition by weight to total protein of the composition by weight ranges from 55:1 to 70:1.

17. A method of manufacturing a composition of matter derived from the lavage of whole lungs, wherein (i) the composition adsorbs to a surface and decreases the surface tension of physiological saline to an equilibrium surface tension within 10 seconds, (ii) the minimum surface tension of the composition is less than 2.1 mN/m at a surface area compression of 50% by the pulsating bubble method of Enhorning at total lipid concentrations of less than 10 mg/ml of the composition; and (iii) the composition restores the pressure-volume mechanics of surface deficient lung by more than 75% of the lost lung volume in the excised lung test of Bermel, comprising the steps of:
    (a) extracting organic soluble materials from the lavage by using at least one organic solvent;
    (b) evaporating the organic solvent;
    (c) suspending the organic soluble materials in an aqueous solvent, thereby forming a suspension;
    (d) agitating the suspension while maintaining the suspension at a temperature greater than 40 degrees centigrade; and
    (e) cooling the suspension.

18. The method of manufacturing the composition as set forth in claim 17, further comprising the step of adding further phospholipid.

19. A method of manufacturing a composition of matter derived from the lavage of whole lungs, wherein (i) the composition adsorbs to a surface and decreases the surface tension of physiological saline to an equilibrium surface tension within 10 seconds; (ii) the minimum surface tension of the composition is less than 2.1 mN/m at a surface area compression of 50% by the pulsating bubble method of Enhorning at total lipid concentrations of less than 5 mg/ml of the compositions and (iii) the composition restores the pressure-volume mechanics of surface deficient lung by more than 75% of the lost lung volume in the excised lung test of Bermel, comprising the steps of:
    (a) extracting organic soluble materials from the lavage by using at least one organic solvent;
    (b) evaporating the organic solvent;
    (c) suspending the organic soluble materials in an aqueous solvent, thereby forming a suspension;
    (d) agitating the suspension while maintaining the suspension at a temperature greater than 40 degrees centigrade; and
    (e) cooling the suspension.

20. The method of manufacturing the composition as set forth in claim 19, further comprising the step of adding further phospholipid.

21. A method of manufacturing a composition of matter derived from the lavage of whole lungs, wherein (i) the composition adsorbs to a surface and decreases the surface tension of physiological saline to an equilibrium surface tension within 10 seconds; (ii) the minimum surface tension of the composition is less than 2.1 mN/m at a surface area compression of 50% by the pulsating bubble method of Enhoming at total lipid concentrations of less than 2 mg/ml of the compositions and (iii) the composition restores the pressure-volume mechanics of surface deficient lung by more than 75% of the lost lung volume in the excised lung test of Bermel, comprising the steps of:

(a) extracting organic soluble materials from the lavage by using at least one organic solvent;

(b) evaporating the organic solvent;

(c) suspending the organic soluble materials in an aqueous solvent, thereby forming a suspension;

(d) agitating the suspension while maintaining the suspension at a temperature greater than 40 degrees centigrade; and (e) cooling the suspension.

22. The method of manufacturing the composition as set forth in claim 21, further comprising the step of adding further phospholipid.

23. The method according to claim 18, 20, or 22 wherein the step of adding the further phospholipid further comprises the step of adding the further phospholipid to the organic soluble materials before evaporating the organic solvent.

24. The method according to claim 18, 20, or 22 wherein the step of adding the further phospholipid further comprises the step of adding the further phospholipid to the suspension.

25. The method according to claim 17, 18, 19, 20, 21, or 22 wherein the evaporating step further comprises the step of creating a vacuum in a space immediately above the organic solvent.

26. The method according to claim 17, 18, 19, 20, 21, or 22 wherein the evaporating step further comprises the step of heating the organic solvent to a temperature greater than the boiling point of the organic solvent.

27. The method according to claim 17, 18, 19, 20, 21, or 22 wherein the agitating step further comprises the step of adding a gas to a space directly above the suspension.

28. The method according to claim 27 wherein the gas is nitrogen.

29. The method according to claim 17, 18, 19, 20, 21, or 22 wherein the agitating step further comprises the step of creating a mechanical vortex.

30. The method of claim 17, 18, 19, 20, 21, or wherein the agitating step further comprises the step of sonicating.

31. The method according to claim 17, 18, 19, 20, 21, or 22 wherein the agitating step further comprises the step of rotating.

32. The method according to claim 17, 18, 19, 20, 21, or 22 wherein the agitating step is performed on the composition while maintaining the composition at a temperature of about 62–99 degrees centigrade.

33. The method according to claim 17, 18, 19, 20, 21, or 22 wherein the agitating step is performed for a time sufficient to remove residual organic solvent from the suspension.

34. The method according to claim 17, 18, 19, 20, 21, or 22 further comprising the step of evaporating the organic solvent in a round bottom flask.

35. The method according to claim 17, 18, 19, 20, 21, or 22 further comprising the step of agitating the suspension in a round bottom flask.

36. The method according to claim 34 wherein the ratio of the mass of the organic-soluble materials to the volume of the round bottom flask is less than about 3.0 grams per liter.

37. The method according to claim 35 wherein the ratio of the mass of the organic-soluble materials to the volume of the round bottom flask is less than about 3.0 grams per liter.

38. The method according to claim 17, 18, 19, 20, 21, or 22 further comprising the steps of:

(a) heating the suspension to a temperature greater than 100 degrees centigrade, and (b) cooling the suspension.

39. The method according to claim 38 wherein the heating step is performed while the suspension is at a pressure greater than 1 atmosphere.

40. The method according to claim 38 further comprising the steps of:

(a) reheating the suspension to greater than 100 degrees centigrade, and (b) after reheating the suspension, recooling the suspension.

41. The method according to claim 40 wherein the recooling step lowers the temperature of the suspension to about 0–10 degrees centigrade.

42. The method according to claim 17, 18, 19, 20, 21, or 22 further comprising the step of sterilizing the suspension.

43. The method according to claim 42 wherein the sterilizing step further comprises the step of heating.

44. The method according to claim 43 wherein the heating step is performed while the suspension is at a pressure greater than 1 atmosphere.

45. The method according to claim 39 wherein the heating step is performed while the suspension is at a temperature of about 121–135 degrees centigrade.

46. The method according to claim 42 wherein the heating step is performed for about 10–60 minutes.

47. A pharmaceutical substance made according to the method of claim 42 which improves lung function in mammalian organisms with lung surfactant deficiency.

48. A pharmaceutical substance made according to the method of claim 42 which improves lung function in mammalian organisms with surfactant dysfunction.

49. A pharmaceutical product comprising the pharmaceutical substance as set forth in claim 47.

50. A pharmaceutical product comprising the pharmaceutical substance as set forth in claim 48.

51. The method of treating with the composition as set forth in claim 13 comprising the step of administering the composition to a mammal suffering from a deficiency of lung surfactant.

52. The method of treating with the composition as set forth in claim 13 comprising the step of administering the composition to a mammal suffering from a dysfunction of lung surfactant.

53. The method of treating with the composition as set forth in claim 13 comprising the step of administering the composition to a mammal suffering from an inhibition of lung surfactant.

54. The method according to claim 51 wherein the administering step further comprises the step of instilling the composition into an airway.

55. The method according to claim 52 wherein the administering step further comprises the step of instilling the composition into an airway.

56. The method according to claim 53 wherein the administering step further comprises the step of instilling the composition into an airway.

57. The method according to claim 54 wherein the instilling step further comprises the step of instilling one or more boluses of the composition.

58. The method according to claim 55 wherein the instilling step further comprises the step of instilling one or more boluses of the composition.

59. The method according to claim 56 wherein the instilling step further comprises the step of instilling one or more boluses of the composition.

60. The method according to claim 54 wherein the instilling step further comprises the step of instilling an aerosol of the composition.

61. The method according to claim 55 wherein the instilling step further comprises the step of instilling an aerosol of the composition.

62. The method according to claim 56 wherein the instilling step further comprises the step of instilling an aerosol of the composition.

63. The method according to claim 54 wherein the instilling step further comprises the step of instilling the composition as a spray.

64. The method according to claim 55 wherein the instilling step further comprises the step of instilling the composition as a spray.

65. The method according to claim 56 wherein the instilling step further comprises the step of instilling the composition as a spray.

66. The method according to claim 51 wherein the administering step further comprises the step of administering the composition to a premature mammal at birth.

67. The method according to claim 52 wherein the administering step further comprises the step of administering the composition to a premature mammal at birth.

68. The method according to claim 53 wherein the administering step further comprises the step of administering the composition to a premature mammal at birth.

69. The method according to claim 51 wherein the administering step further comprises the step of administering the composition to a mammal with a respiratory disease.

70. The method according to claim 52 wherein the administering step further comprises the step of administering the composition to a mammal with a respiratory disease.

71. The method according to claim 53 wherein the administering step further comprises the step of administering the composition to a mammal with a respiratory disease.

72. The method according to claim 51 wherein the administering step further comprises the step of administering the composition to a mammal with a respiratory distress syndrome.

73. The method according to claim 52 wherein the administering step further comprises the step of administering the composition to a mammal with a respiratory distress syndrome.

74. The method according to claim 53 wherein the administering step further comprises the step of administering the composition to a mammal with a respiratory distress syndrome.

75. The method according to claim 51 wherein the administering step further comprises the step of administering the composition to a mammal with respiratory failure.

76. The method according to claim 52 wherein the administering step further comprises the step of administering the composition to a mammal with respiratory failure.

77. The method according to claim 53 wherein the administering step further comprises the step of administering the composition to a mammal with respiratory failure.

78. The method according to claim 51 wherein the administering step further comprises the step of administering the composition to a mammal with inhalation injury to the lung.

79. The method according to claim 52 wherein the administering step further comprises the step of administering the composition to a mammal with inhalation injury to the lung.

80. The method according to claim 53 wherein the administering step further comprises the step of administering the composition to a mammal with inhalation injury to the lung.

81. The method according to claim 51 wherein the administering step further comprises the step of administering the composition to a mammal undergoing a therapy for a disease that has a risk for a respiratory disease due to an abnormality in surfactant function.

82. The method according to claim 52 wherein the administering step further comprises the step of administering the composition to a mammal undergoing a therapy for a disease that has a risk for a respiratory disease due to an abnormality in surfactant function.

83. The method according to claim 53 wherein the administering step further comprises the step of administering the composition to a mammal undergoing a therapy for a disease that has a risk for a respiratory disease due to an abnormality in surfactant function.

\* \* \* \* \*